United States Patent
Fields et al.

(10) Patent No.: US 12,234,514 B2
(45) Date of Patent: Feb. 25, 2025

(54) SOURCE OF ORIGIN DECONVOLUTION BASED ON METHYLATION FRAGMENTS IN CELL-FREE DNA SAMPLES

(71) Applicant: Grail, LLC, Menlo Park, CA (US)

(72) Inventors: Alexander P. Fields, Mountain View, CA (US); Oliver Claude Venn, San Francisco, CA (US); Gordon Cann, Redwood City, CA (US); Samuel S. Gross, Sunnyvale, CA (US); Arash Jamshidi, Redwood City, CA (US)

(73) Assignee: GRAIL, Inc., Menlo Park, CA (US)

( * ) Notice: Subject to any disclaimer, the term of this patent is extended or adjusted under 35 U.S.C. 154(b) by 927 days.

(21) Appl. No.: 16/723,716

(22) Filed: Dec. 20, 2019

(65) Prior Publication Data

US 2020/0239965 A1    Jul. 30, 2020

Related U.S. Application Data

(60) Provisional application No. 62/784,353, filed on Dec. 21, 2018.

(51) Int. Cl.
| | | |
|---|---|---|
| C12Q 1/6886 | (2018.01) | |
| G06F 17/18 | (2006.01) | |
| G16B 5/00 | (2019.01) | |
| G16B 50/10 | (2019.01) | |
| G16B 50/30 | (2019.01) | |

(52) U.S. Cl.
CPC ........... *C12Q 1/6886* (2013.01); *G06F 17/18* (2013.01); *G16B 5/00* (2019.02); *G16B 50/10* (2019.02); *G16B 50/30* (2019.02); *C12Q 2600/154* (2013.01)

(58) Field of Classification Search
CPC .. C12Q 1/6886; C12Q 2600/154; G16B 5/00; G16B 50/30; G16B 50/10; G06F 17/18
See application file for complete search history.

(56) References Cited

U.S. PATENT DOCUMENTS

| | | | |
|---|---|---|---|
| 8,415,100 | B2 | 4/2013 | Markowitz et al. |
| 8,900,829 | B2 | 12/2014 | Distler et al. |
| 9,580,754 | B2 | 2/2017 | Markowitz et al. |
| 9,984,201 | B2 | 5/2018 | Zhang et al. |
| 10,731,215 | B2 | 8/2020 | Ballhause et al. |
| 2005/0221314 | A1 | 10/2005 | Berlin et al. |
| 2011/0028333 | A1 | 2/2011 | Christensen et al. |
| 2011/0059432 | A1 | 3/2011 | Ballhause et al. |
| 2012/0041683 | A1 | 2/2012 | Vaske et al. |
| 2013/0079241 | A1 | 3/2013 | Luo et al. |
| 2014/0080715 | A1 | 3/2014 | Lo et al. |
| 2014/0127688 | A1 | 5/2014 | Umbarger et al. |
| 2015/0299809 | A1 | 10/2015 | Hansen et al. |
| 2016/0017419 | A1 | 1/2016 | Chiu et al. |
| 2016/0017430 | A1 | 1/2016 | Badosa |
| 2016/0210403 | A1 | 7/2016 | Zhang et al. |
| 2016/0340740 | A1 | 11/2016 | Zhang |
| 2016/0340749 | A1 | 11/2016 | Stelzer et al. |
| 2017/0121767 | A1 | 5/2017 | Dor et al. |
| 2017/0175205 | A1 | 6/2017 | Toung et al. |
| 2018/0010192 | A1 | 1/2018 | Zhang et al. |
| 2018/0143198 | A1 | 5/2018 | Wen et al. |
| 2018/0216195 | A1 | 8/2018 | Elnitski et al. |
| 2018/0237867 | A1 | 8/2018 | Bajic et al. |
| 2018/0327859 | A1 | 11/2018 | Van Engeland et al. |
| 2018/0334715 | A1 | 11/2018 | Gromminger et al. |
| 2018/0341745 | A1 | 11/2018 | Zhang et al. |
| 2019/0032149 | A1 | 1/2019 | Van Engeland et al. |
| 2019/0161805 | A1 | 5/2019 | Ahlquist et al. |
| 2019/0161806 | A1 | 5/2019 | Ahlquist et al. |
| 2019/0256924 | A1 | 8/2019 | Vogelstein et al. |

(Continued)

FOREIGN PATENT DOCUMENTS

| | | |
|---|---|---|
| EP | 1342794 B1 | 12/2005 |
| EP | 1394173 B1 | 10/2007 |
| EP | 1871912 B1 | 2/2012 |

(Continued)

OTHER PUBLICATIONS

Kang, S. et al., "CancerLocator: non-invasive cancer diagnosis and tissue-of-origin prediction using methylation profiles of cell-free DNA," Genome Biology, vol. 18, No. 53, 2017, pp. 1191-1195.
PCT International Search Report and Opinion, PCT Application No. PCT/US2019/068060, Apr. 17, 2020, 19 pages.
PCT International Search Report and Opinion, PCT Application No. PCT/US2019/068014, Apr. 17, 2020, 17 pages.
Shen, S. Y. et al., "Sensitive tumour detection and classification using plasma cell-free DNA methylomes," Nature, vol. 563, Nov. 22, 2018, pp. 579-583.

(Continued)

*Primary Examiner* — Mark Halvorson
*Assistant Examiner* — Dennis J Sullivan
(74) *Attorney, Agent, or Firm* — Fenwick & West LLP

(57) ABSTRACT

A method and system for determining one or more sources of a cell free deoxyribonucleic acid (cfDNA) test sample from a test subject. The cfDNA test sample contains a plurality of deoxyribonucleic acid (DNA) molecules with numerous CpG sites that may be methylated or unmethylated. A trained deconvolution model comprises a plurality of methylation parameters, including a methylation level at each CpG site for each source, and a function relating a sample vector as input and a source of origin prediction as output. The method generates a test sample vector comprising a site methylation metric relating to DNA molecules from the test sample that are methylated at that CpG site. The method inputs the test sample vector into the trained deconvolution model to generate a source of origin prediction indicating a predicted DNA molecule contribution of each source.

17 Claims, 19 Drawing Sheets

(56) References Cited

U.S. PATENT DOCUMENTS

| | | |
|---|---|---|
| 2020/0048697 A1 | 2/2020 | Liu |
| 2020/0291459 A1 | 9/2020 | Domanico et al. |

FOREIGN PATENT DOCUMENTS

| | | | |
|---|---|---|---|
| EP | 2380993 B1 | 12/2015 | |
| EP | 2670893 B1 | 6/2018 | |
| EP | 3336197 A1 | 6/2018 | |
| EP | 3230476 B1 | 2/2020 | |
| EP | 3390657 B1 | 9/2020 | |
| WO | WO 2004/046332 A2 | 6/2004 | |
| WO | WO 2005/019477 A2 | 3/2005 | |
| WO | WO 2006/113770 A1 | 10/2006 | |
| WO | WO 2007/132167 A2 | 11/2007 | |
| WO | WO 2008/084219 A1 | 7/2008 | |
| WO | WO 2011/038507 A1 | 4/2011 | |
| WO | WO 2011/091046 A1 | 7/2011 | |
| WO | WO 2011/092592 A2 | 8/2011 | |
| WO | WO 2011/130751 A1 | 10/2011 | |
| WO | WO 2012/031329 A1 | 3/2012 | |
| WO | WO 2012/071621 A1 | 6/2012 | |
| WO | WO 2012/103031 A2 | 8/2012 | |
| WO | WO 2012/106525 A2 | 8/2012 | |
| WO | WO 2013/066641 A1 | 5/2013 | |
| WO | WO 2013/116375 A1 | 8/2013 | |
| WO | WO 2014/043763 A1 | 3/2014 | |
| WO | WO 2015/116837 A1 | 8/2015 | |
| WO | WO 2015/159292 A2 | 10/2015 | |
| WO | WO 2016/094839 A2 | 6/2016 | |
| WO | WO 2016/101258 A1 | 6/2016 | |
| WO | WO 2016/115530 A1 | 7/2016 | |
| WO | WO 2017/075061 A1 | 5/2017 | |
| WO | WO 2017/106481 A1 | 6/2017 | |
| WO | WO 2017/212428 A1 | 12/2017 | |
| WO | WO 2018/109217 A1 | 6/2018 | |
| WO | WO 2018/119216 A1 | 6/2018 | |
| WO | WO 2018/165366 A1 | 9/2018 | |
| WO | WO-2018161031 A1 * | 9/2018 | ........... C12Q 1/6886 |
| WO | WO 2018/195211 A1 | 10/2018 | |
| WO | WO 2018/195217 A1 | 10/2018 | |
| WO | WO 2019/064063 A1 | 4/2019 | |
| WO | WO 2019/067092 A1 | 4/2019 | |
| WO | WO 2019/199696 A1 | 10/2019 | |

OTHER PUBLICATIONS

Grail, Inc., "The Circulating Cell-free Genome Atlas Study (CCGA)," ClinicalTrials.gov Identifier: NCT02889978, Feb. 11, 2019, six pages, [Online] [Retrieved on Apr. 3, 2020] Retrieved from the Internet <URL: https://www.clinicaltrials.gov/ct2/show/NCT02889978>.

Guo, S. et al., "Identification of methylation haplotype blocks aids in deconvolution of heterogeneous tissue samples and tumor tissue-of-origin mapping from plasma DNA," Nature Genetics, vol. 49, No. 4. Apr. 2017, pp. 635-644.

"IHEC—International Human Epigenome Consortium,", Date Unknown, four pages, [Online] [Retrieved on Apr. 3, 2020] Retrieved from the Internet <URL.

Milani, L. et al., "DNA methylation for subtype classification and prediction of treatment outcome in patients with childhood acute lymphoblastic leukemia," Blood, vol. 115, No. 6, Feb. 11, 2010, pp. 1214-1225.

PCT International Search Report and Written Opinion, PCT Application No. PCT/US2019/022122, Aug. 23, 2019, 25 pages.

PCT Invitation to Pay, PCT Application No. PCT/US2019/022122, Jul. 1, 2019, 23 pages.

Xu, R. et al., "Circulating tumour DNA methylation markers for diagnosis and prognosis of hepatocellular carcinoma," Nature Materials, Oct. 9, 2017, pp. 1-8.

Bibikova, M. et al., "High-throughput DNA methylation profiling using universal bead arrays," Genome Research, vol. 16, Jan. 31, 2006, pp. 383-393.

Broquet, T. et al., "Quantifying genotyping errors in noninvasive population genetics," Molecular Ecology, Oct. 2004, pp. 3601-3608.

Chan, K.C.A. et al., "Noninvasive detection of cancer-associated genome-wide hypomethylation and copy number aberrations by plasma DNA bisulfite sequencing," PNAS, vol. 110, No. 47, Nov. 19, 2013 pp. 18761-18768.

Chimonidou, M. et al., "SOX17 Promoter Methylation in Circulating Tumor Cells and Matched Cell-Free DNA Isolated from Plasma of Patients with Breast Cancer," Clinical Chemistry 59(1), Jan. 2013, pp. 270-279.

Chu, W-T., "Chapter 12 Solving Linear Equations," An Introduction to Optimization, Spring 2014, pp. 1-47.

Cipriany, B.R. et al., "Single Molecule Epigenetic Analysis in a Nanofluidic Channel," Analytical Chemistry, vol. 82, No. 6, Mar. 15, 2010, pp. 2480-2487.

Coolen, M.W. et al., "Genomic profiling of CpG methylation and allelic specificity using quantitative high-throughput mass spectrometry: critical evaluation and improvements," Nucleic Acids Research, vol. 35, No. 18, e119, Sep. 13, 2007, pp. 1-14.

Da Costa, A.N. et al., "Detection of cancer-specific epigenomic changes in biofluids: Powerful tools in biomarker discovery and application," Molecular Oncology, vol. 6, Iss. 6, Dec. 2012, pp. 704-715.

De Martino, M. et al., "Serum Cell-Free DNA in Renal Cell Carcinoma: A diagnostic and prognostic marker," Cancer, vol. 118, Iss. 1, Jun. 28, 2011, pp. 82-90.

Ehrlich, M., "DNA methylation in cancer: too much, but also too little," Oncogene, vol. 21, Aug. 5, 2002, pp. 5400-5413.

Fackler, M.J. et al., "Quantitative Multiplex Methylation-Specific PCR Assay for the Detection of Promoter Hypermethylation in Multiple Genes in Breast Cancer," Cancer Research, vol. 64, Iss. 13, Jul. 2004, pp. 4442-4452.

Flanagan, J.M. et al., "DNA methylome of familial breast cancer identifies distinct profiles defined by mutation status," The American Journal of Human Genetics, vol. 86, Mar. 12, 2010, pp. 420-433.

Flusberg, B.A. et al., "Direct detection of DNA methylation during single-molecule, real-time sequencing," Nature Methods, vol. 7, No. 6, Jun. 2010, pp. 461-467.

Holmes, E.E. et al., "Performance Evaluation of Kits for Bisulfite-Conversion from DNA Tissues, Cell Lines, FFPE Tissues, Aspirates, Lavages, Effusions, Plasma, Serum and Urine," PLoS One, vol. 9, Iss. 4, Apr. 3, 2014, pp. 1-15.

Houseman, E.A. et al., "Reference-free cell mixture adjustments in analysis of DNA methylation data," Bioinformatics, vol. 30, No. 10, Jan. 21, 2014, pp. 1431-1449.

Jin, H. et al., "Chapter 6: Circulating methylated DNA as biomarkers for cancer detection," Methylation—From DNA, RNA and Histones to Diseases and Treatment, Nov. 2012, pp. 137-152.

Kadam, S.K. et al., "Quantitative Measurement of Cell-Free Plasma DNA and Applications for Detecting Tumor Genetic Variation and Promoter Methylation in a Clinical Setting," The Journal of Molecular Diagnostics, vol. 14, No. 4, Jul. 2012, pp. 346-356.

Kit, A.H. et al., "DNA Methylation based biomarkers; Practical considerations and applications," Biochimie, vol. 94, Jul. 27, 2012, pp. 2314-2337.

Kuo, H.C. et al., "DBCAT: database of CpG island and analytical tools for identifying comprehensive methylation profiles in cancer cells," Journal of Computational Biology, vol. 18, No. 8, Jul. 29, 2011, pp. 1013-1017.

Laird, P.W., "Principles and Challenges of genome-wide DNA methylation analysis," Nature Reviews Genetics, vol. 11, Feb. 2, 2010, pp. 191-203.

Lee, E.J. et al., "Analyzing the cancer methylome through targeted bisulfite sequencing," Cancer Letters, vol. 340, Nov. 2013, pp. 171-178.

Legendre, C. et al., "Whole-genome bisulfite sequencing of cell-free DNA identifies signature associated with metastatic breast cancer," Clinical Epigenetics, vol. 7, Sep. 16, 2015, pp. 1-10.

Li, W. et al., "CancerDetector: ultrasensitive and non-invasive cancer detection at the resolution of individual reads using cell-free

(56) References Cited

OTHER PUBLICATIONS

DNA methylation sequencing data," Nucleic Acids Research, vol. 46, No. 15, Jun. 12, 2018, pp. 1-11.
Liggett, T.E. et al., "Distinctive DNA methylation patterns of cell-free plasma DNA in women with malignant ovarian tumors," Gynecologic Oncology, vol. 120, Jan. 2011, pp. 113-120.
Lo, Y.M.D. et al., "Genomic Analysis of Fetal Nucleic Acids in Maternal Blood," Annual Review Genomics and Human Genetics, vol. 13, Sep. 2012, pp. 285-306.
Lo, Y.M.D. et al., "Maternal plasma DNA sequencing reveals the genome-wide genetic and mutational profile of the fetus," Science Translational Medicine, vol. 2, Iss. 61, Dec. 8, 2010, pp. 1-13.
Miller, C.A. et al., "ReadDepth: A parallel R package for detecting copy number alterations from short sequencing reads," PLOS One, vol. 6, Iss. 1, Jan. 31, 2011, pp. 1-7.
Ogoshi, K. et al., "Genome-wide profiling of DNA methylation in human cancer cells," Genomics, vol. 98, Iss. 4, Oct. 2011, pp. 280-287.
O'Sullivan, E. et al., "DNA methylation analysis in human cancer," Pancreatic Cancer: Methods and Protocols, Methods in Molecular Biology, vol. 980, Dec. 13, 2012, pp. 131-156.
Page, K. et al., "Detection of HER2 amplification in circulating free DNA in patients with breast cancer," British Journal of Cancer, vol. 104, Mar. 22, 2011, pp. 1342-1348.
Pedersen, I.S. et al., "High recovery of cell-free methylated DNA based on a rapid bisulfite-treatment protocol," BMC Molecular Biology, vol. 13, Mar. 26, 2012, pp. 1-8.
Price, E.M. et al., "Different measures of "genome-wide" DNA methylation exhibit unique properties in placental and somatic tissues," Epigenetics, vol. 7, Iss. 6, Jun. 2012, pp. 652-663.
Quackenbush, J., "Microarray data normalization and transformation," Nature Genetics Supplement, vol. 32, Dec. 2002, pp. 496-501.
Radpour, R. et al., "Hypermethylation of tumor suppressor genes involved in ciritical regulatory pathways for developing a blood-based test in breast cancer," PLOS One, vol. 6, Iss. 1, Jan. 24, 2011, pp. 1-11.
Robinson, M.D. et al. "Evaluation of affinity-based genome-wide DNA methylation data: Effects of CpG density, amplification bias, and copy number variation," Genome Research, vol. 20, Nov. 2, 2010, pp. 1718-1729.
Saied, M.H. et al., "Genome wide analysis of acute myeloid leukemia reveal leukemia specific methylome and subtype specific hypomethylation of repeats," PloS One, vol. 7, No. 3, Mar. 29, 2012, pp. 1-12.
Schwarzenbach, H. et al., "Cell-free nucleic acids as biomarkers in cancer patients," Nature Reviews Cancer, May 12, 2011, pp. 1-12.
Shaw, J.A. et al., "Genomic analysis of circulating cell free DNA infers breast cancer dormancy," Genome Research, vol. 22, Oct. 11, 2011, pp. 220-231.
Tanic, M. et al., "Epigenome-wide association studies for cancer biomarker discovery in circulating cell-free DNA: technical advances and challenges," Current Opinion in Genetics & Development, vol. 42, Feb. 2017, pp. 48-55.

Van De Voorde, L. et al., "DNA methylation-based biomarkers in serum of patients with breast cancer," Mutation Research, vol. 751, Jun. 12, 2012, pp. 304-325.
Weisenberger, D.J. et al., "DNA methylation analysis by digital bisulfite genomic sequencing and digital MethyLight," Nucleic Acids Research, vol. 36, No. 14, Jul. 15, 2008, pp. 4689-4698.
Wu, G. et al., "Statistical Quantification of Methylation Levels by Next-Generation Sequencing," PLoS One, vol. 6, Iss. 6, Jun. 15, 2011, pp. 1-12.
Yu, M. et al., "Tet-assisted bisulfite sequencing of 5-hydroxyethylcyctosine," Nature Protocols, vol. 7, No. 12, Nov. 29, 2012, pp. 2159-2170.
Yuen, R.K.C. et al., "Genome-wide mapping of imprinted differentially methylated regions of DNA methylation profiling of human placentas from triploidies," Epigenetics & Chromatin, vol. 4, Article No. 10, Jul. 13, 2011, pp. 1-16.
Zhai, R. et al., "Genome-wide DNA Methylation Profiling of Cell-Free Serum DNA in Esophageal Adenocarcinoma and Barrett Esophagus," Neoplasia 14(1), Jan. 2012, pp. 29-33.
Baumann, D. et. al, "MAGI Methylation Analysis Using Genome Information," Epigenetics, vol. 9, Issue 5, Mar. 31, 2014, pp. 698-703.
Kreuger, F. et. al, "Bismark: A Flexible Aligner and Methylation Caller for Bisulfite-Seq Applications," Bioinformatics, vol. 27, Issue 11, Jun. 1, 2011, pp. 1571-1572.
Shen, L. et al. "Detect Differentially Methylated Regions Using Non-Homogenous Hidden Markov Model for Methylation Array Data," Bioinformatics, vol. 33, Issue 23, Dec. 1, 2017, pp. 3701-3708.
United States Office Action, U.S. Appl. No. 16/352,602, filed Apr. 19, 2022, 25 pages.
Angermueller, C. et al., "DeepCpG: accurate prediction of single-cell DNA methylation states using deep learning," Genome Biology, 18(1), Apr. 11, 2017, 13 pages.
Khwaja, M. et al., "A Deep Autoencoder System for Differentiation of Cancer Types Based on DNA Methylation State," Oct. 5, 2018, pp. 1-8.
Margolin, G. et al., "Robust detection of DNA hypermethylation of ZNF154 as a pan-cancer locus with in silico modeling for blood-based diagnostic development," Journal of Molecular Diagnostics, 18.2, Mar. 2016, pp. 283-298.
Taiwan Intellectual Property Office, Office Action, TW Patent Application No. 108108527, Mar. 6, 2023, nine pages.
United States Office Action, U.S. Appl. No. 16/352,602, filed Dec. 15, 2022, 17 pages.
United States Office Action, U.S. Appl. No. 16/723,411, filed Apr. 13, 2023, 42 pages.
Wu, H. et al., "Redefining CpG islands using hidden Markov models," Biostatistics, 11(3), Mar. 8, 2010, pp. 499-514.
Yassi, M. et al., "DMRFusion: a differentially methylated region detection tool based on the ranked fusion method," Genomics 110.6, Jan. 5, 2018, pp. 366-374.

\* cited by examiner

Calculating sample vector [$\beta_{N, sample}$] for
deconvolution model
200

Generate set of methylation state vectors from a
sample
100

Remove questionable methylation state vectors
from the sample
210

For each CpG site [n], identify methylation state
vectors inclusive of that CpG site [n]
220

For each CpG site [n], calculate a methylation
metric [$\beta_{n, sample}$] corresponding to a percentage of
identified methylation state vectors inclusive of
that CpG site [n] that are methylated
230

Generate sample vector [$\beta_{N, sample}$] inclusive of
methylation metrics at each CpG site
240

FIG. 2A

Generate data structure for a control group
250

Generate set of methylation state vectors
for a control group
100

For each methylation state vector, subdivide into
strings of methylation sites
255

Tally strings for each position and methylation
state combination
260

Create data structure storing counts of all
possible strings from the control group
265

FIG. 2B

Training a Deconvolution Model
300

Obtain a plurality of training samples from a plurality of sources [K], each training sample comprising a training sample vector [$\beta_{N, training}$]
305

Generate, for each source [k] at each CpG site [n] of a plurality of CpG sites [N], a methylation parameter [$\beta_{n, k}$] based on the training sample vectors [$\beta_{N, training}$] for training samples of that source [k]
310

Calculate an information gain for each CpG site [n] of the plurality of CpG sites [N] based on the methylation parameters [$\beta_{N, K}$]
315

Select a subset of CpG sites [N'] of the CpG sites [N] for use in the deconvolution model based on the information gain
320

FIG. 3A

Deployment of Deconvolution Model
330

Obtain a test sample with DNA fragments from a plurality of sources [K], the test sample having a test sample vector [$\beta_{N, test}$]
335

Input the test sample vector [$\beta_{N, test}$] into a deconvolution model
340

Determine a source of origin prediction [$f_K$] with the function of the deconvolution model, the function representing a relation between the test sample vector [$\beta_{N, test}$] received as input and the source of origin prediction [$f_K$] as output, the source of origin prediction [$f_K$] based on the test sample vector [$\beta_{N, test}$] and the methylation parameters [$\beta_{N, K}$]
345

FIG. 3B

SOURCE OF ORIGIN DECONVOLUTION BASED ON METHYLATION FRAGMENTS IN CELL-FREE DNA SAMPLES

CROSS-REFERENCE TO RELATED APPLICATIONS

This application claims the benefit of priority to U.S. Provisional Patent Application No. 62/784,353, filed on Dec. 21, 2018, and entitled "Source of Origin Deconvolution Based on Methylation Fragments in Cell-Free DNA Samples", which is incorporated by reference in its entirety.

This application is related to and incorporates the entirety of U.S. patent application Ser. No. 16/352,602, filed on Mar. 13, 2019, and entitled "Anomalous Fragment Detection and Classification".

This application is related to and incorporates the entirety of U.S. patent application Ser. No. 16/723,411, filed on Dec. 20, 2019, and entitled "Anomalous Fragment Detection and Classification".

BACKGROUND

Field of Art

Deoxyribonucleic acid (DNA) methylation plays an important role in regulating gene expression. Aberrant DNA methylation has been implicated in many disease processes, including cancer. DNA methylation profiling using methylation sequencing (e.g., whole genome bisulfite sequencing (WGBS)) is increasingly recognized as a valuable diagnostic tool for detection, diagnosis, and/or monitoring of cancer. For example, specific patterns of differentially methylated regions and/or allele specific methylation patterns may be useful as molecular markers for non-invasive diagnostics using circulating cell-free (cf) DNA. However, there remains a need in the art for improved methods for analyzing methylation sequencing data from cell-free DNA for the detection, diagnosis, and/or monitoring of diseases, such as cancer.

SUMMARY

Early detection of cancer in subjects is important as it allows for earlier treatment and therefore a greater chance for survival. Sequencing of fragments of cell-free (cf) DNA to compare methylation states of various dinucleotides of cytosine and guanine (known as CpG sites) in the fragments provides insight into whether a subject has cancer, and further insight on what type of cancer the subject may have. Towards that end, this description includes methods for analyzing methylation states of CpG sites of cfDNA for determining.

In one embodiment, a deconvolution model is trained to generate source of origin predictions. Training data is first obtained which includes training samples from a multitude of sources. Each training sample includes cfDNA that originates from one source of the multitude of sources. The cfDNA further includes numerous methylation fragments, each with a methylation state for each CpG site on the methylation fragment. A sample vector is calculated for each training sample—i.e. a training sample vector—by determining a methylation level at each CpG site. The methylation level is determined by aggregating the methylation states of the methylation fragments in the training sample. The deconvolution model accumulates a plurality of methylation parameters which describe a methylation level at each CpG site of a plurality of CpG sites for each source of a plurality of sources. The deconvolution model further uses a function that calculates the source of origin predictions based on the methylation parameters and test samples.

For a test sample, a deconvolution method generates a source of origin prediction using the deconvolution model. The test sample contains cfDNA from a subject, wherein the cfDNA includes DNA molecules. The DNA molecules are processed and read as sequence reads or fragments and methylation status determined at one or more methylation sites (e.g., one or more CpG sites). A sample vector is calculated for the test sample—i.e. a test sample vector—by determining a methylation level at each CpG site. The methylation level is determined by aggregating the methylation states of the methylation fragments in the test sample. The test sample vector is then input into the deconvolution model. The deconvolution model uses the function to generate a source of origin prediction based on the methylation parameters and the test sample vector. In some examples, each value in the source of origin prediction indicates a percentage of the methylation fragments in the test sample likely originating from a source.

In one embodiment, a classifier determines a cancer prediction based on the source of origin prediction for a test sample. Training samples for the classifier each have a source of origin prediction with a label indicating whether the training sample has cancer or not. The classifier then trains classification parameters and a function based on the training samples. Once trained, the classifier receives a source of origin prediction for a test sample and determines a cancer prediction with the classification parameters and the function representing a relation between the source of origin prediction for the test sample received as input and the cancer prediction provided as output based on the parameters and the function. The cancer prediction may include a plurality of cancer prediction values, each cancer prediction value describing a likelihood that the test sample is of a particular cancer type of a plurality of cancer types.

In a further embodiment, the trained cancer classifier comprises a plurality of classification parameters trained on a second set of training samples, each training sample in the second set comprising a label indicating whether the training sample has cancer or does not have cancer, a training source of origin indicating one of the sources that the sample originates from, and a second function representing a relation between the source of origin prediction received as input and the cancer prediction provided as output based on the classification parameters and the second function.

In a further embodiment, the cancer types include a breast cancer type, a colorectal cancer type, an esophageal cancer type, a head/neck cancer type, a hepatobiliary cancer type, a lung cancer type, a lymphoma cancer type, an ovarian cancer type, a pancreas cancer type an anorectal cancer type, a cervical cancer type, a gastric cancer type, a leukemia cancer type, a multiple myeloma cancer type, a prostate cancer type, a renal cancer type, a thyroid cancer type, a uterine cancer type, a brain cancer type, a sarcoma cancer type, a neuroendocrine cancer type.

In a further embodiment, the trained cancer classifier is a multinomial logistic regression classifier.

In a further embodiment, the trained cancer classifier is a logistic regression classifier.

In a further embodiment, the trained deconvolution model comprises a plurality of methylation parameters, wherein the methylation parameters comprise a methylation level at each of the plurality of CpG sites for each of the plurality of sources, and a function representing a relation between the test sample vector received as input and the source of origin prediction generated as output based on the test sample vector and the plurality of methylation parameters.

In a further embodiment, the plurality of methylation parameters are generated from a first set of training samples from the plurality of sources.

In a further embodiment, the first set of training samples is obtained from healthy individuals.

In a further embodiment, the methylation parameters are trained on information comprising the first set of training samples from the plurality of sources, each of the training samples from a source of the plurality of sources comprising a training sample vector comprising a plurality of methylation metrics for each of the plurality of CpG sites, and an identification of the source the training sample originates from.

In a further embodiment, the trained deconvolution model is trained using a minimization function configured to reduce a least squares difference between each training sample and a matrix product of the methylation parameters and a vector of values representing the source of the training sample.

In a further embodiment, the CpG sites used in the trained deconvolution model are identified according to steps of for each of an initial set of CpG sites, computing information gain for deriving one or more sources of the plurality of sources; and identifying a plurality of informative CpG sites to be used in the trained model from the initial set of CpG sites based on the computed information gain of each CpG site.

In a further embodiment, the CpG sites used in the trained deconvolution model are identified according to additional steps of ranking the initial set of CpG sites based on the computed information gain, and wherein identifying the informative CpG sites to be used in the trained model is based on the ranking of the initial set of CpG sites.

In a further embodiment, each source of the plurality of sources is of a tissue type.

In a further embodiment, the plurality of sources comprises any combination of a large intestine tissue type, a breast tissue type, a thyroid tissue type, a lung tissue type, a bladder tissue type, a cervix tissue type, and a colorectal tissue type.

In a further embodiment, the plurality of sources further comprises any combination of an esophagus tissue type, a gastric tissue type, a tonsil tissue type, a liver tissue type, a white blood cell tissue type, an ovary tissue type, a pancreas tissue type, a prostate tissue type, a kidney tissue type, a thyroid tissue type, and a uterus tissue type.

In a further embodiment, each source of the plurality of sources is of a cell type.

In a further embodiment, the plurality of sources comprises any combination of a B cell type, a dendritic cell type, an endothelial cell type, an eosinophil cell type, an erythroblast cell type, a macrophage cell type, a megakaryocyte cell type, a monocyte cell type, a natural killer cell type, a neutrophil cell type, a precursor B cell type, a T cell type, a thymocyte cell type, an adipocyte cell type, a hepatocyte cell type, an islet cell type, and a preadipocyte cell type.

In a further embodiment, the plurality of sources comprises any combination of a large intestine tissue type, a breast tissue type, a thyroid tissue type, a lung tissue type, a bladder tissue type, a cervix tissue type, a colorectal tissue type, an esophagus tissue type, a gastric tissue type, a tonsil tissue type, a liver tissue type, a white blood cell tissue type, an ovary tissue type, a pancreas tissue type, a prostate tissue type, a kidney tissue type, a thyroid tissue type, a uterus tissue type, a B cell type, a dendritic cell type, an endothelial cell type, an eosinophil cell type, an erythroblast cell type, a macrophage cell type, a megakaryocyte cell type, a monocyte cell type, a natural killer cell type, a neutrophil cell type, a precursor B cell type, a T cell type, a thymocyte cell type, an adipocyte cell type, a hepatocyte cell type, an islet cell type, and a preadipocyte cell type.

In a further embodiment, each DNA fragment of a plurality of the set of fragments is an anomalous fragment, wherein an anomalous fragment is identified by filtering an initial set of fragments using p-value filtering to generate the set of anomalous fragments, the filtering comprising removing fragments from the initial set having below a threshold p-value to produce the set of anomalous fragments.

In a further embodiment, each fragment of a plurality of the set of fragments is also hypomethylated or hypermethylated such that the fragment includes at least a threshold number of CpG sites with more than a threshold percentage of the CpG sites being unmethylated or with more than the threshold percentage of the CpG sites being methylated, respectively.

BRIEF DESCRIPTION OF DRAWINGS

FIG. 2A is a flowchart describing a process of calculating sample vectors for a deconvolution model, according to an embodiment.

FIG. 2B is a flowchart describing a process of generating a data structure for a healthy control group, according to an embodiment.

FIG. 3A is a flowchart describing a process of training a deconvolution model, according to an embodiment.

FIG. 3B is a flowchart describing a process of generating a source of origin prediction using a deconvolution model, according to an embodiment.

Figure 1A:
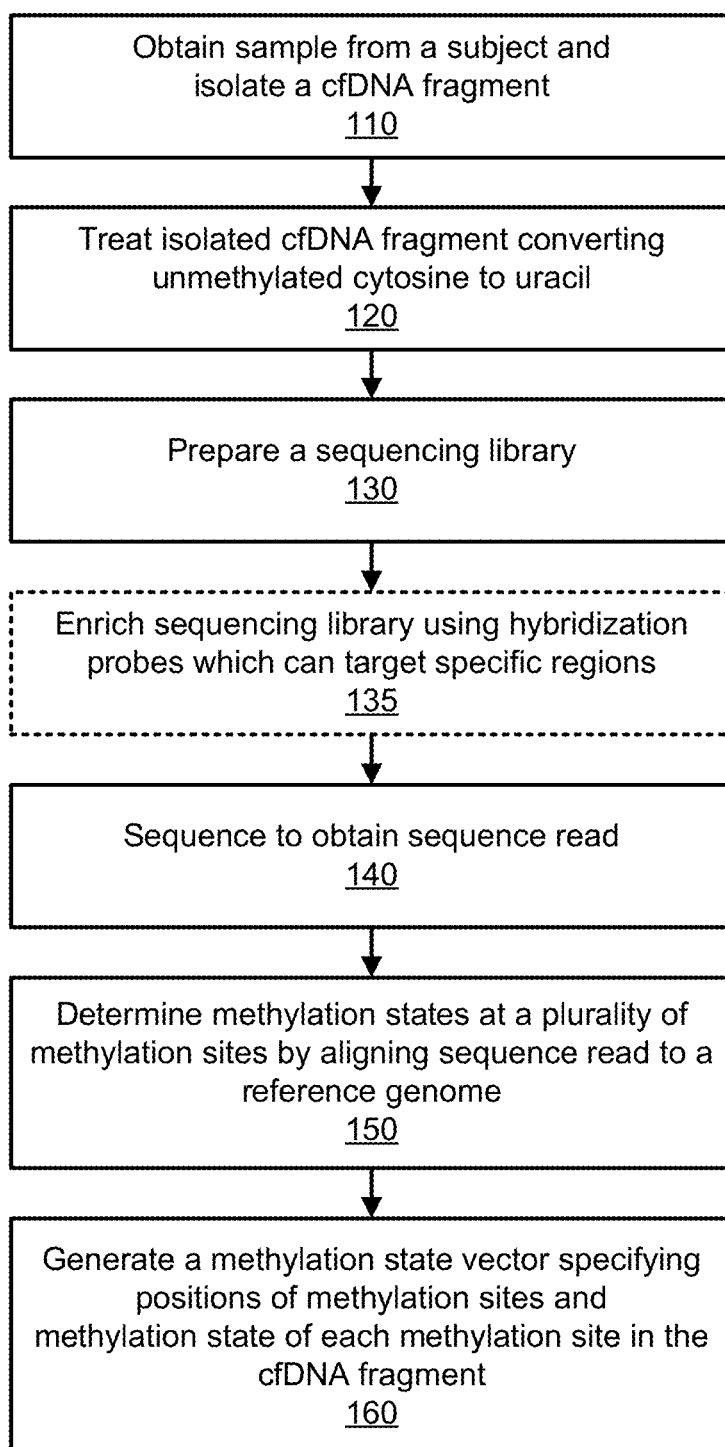
FIG. 1A is a flowchart describing a process of sequencing a fragment of cell-free (cf) DNA to obtain a methylation state vector, according to an embodiment.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

I. Overview

I.A. Overview of Methylation

In accordance with the present description, cfDNA molecules from a test subject are treated, for example by converting unmethylated cytosines to uracils, sequenced and the sequence reads compared to a reference genome to identify the methylation states at specific CpG sites within the fragments. Each CpG site may be methylated or unmethylated. As each source of cfDNA molecules have varying methylation patterns and signatures, deconvolution of a test subject's cfDNA molecules may provide insight as to fractional contributions of cfDNA from among the many possible sources. In individuals with cancer, cfDNA molecules may originate from tumorous cells, and those cfDNA molecules collectively may include cancer specific methylation markers, cancer type specific methylation markers, source specific methylation markers. Additionally, cfDNA molecules may also originate from non-tumorous cells surrounding the tumorous cells due to increased inflammation, necrosis, etc. caused by the tumor. The cfDNA from these non-tumorous cells may also contain source specific methylation markers which can be linked back to the source of the cancer.

Methylation typically occurs in deoxyribonucleic acid (DNA) when a hydrogen atom on the pyrimidine ring of a cytosine base is converted to a methyl group, forming 5-methylcytosine. In particular, methylation tends to occur at dinucleotides of cytosine and guanine referred to herein as "CpG sites". In other instances, methylation may occur at a cytosine not part of a CpG site or at another nucleotide that is not cytosine; however, these are rarer occurrences. In this present disclosure, methylation is discussed in reference to CpG sites for the sake of clarity.

Those of skill in the art will appreciate that the principles described herein are equally applicable for the detection of methylation in a non-CpG context, including non-cytosine methylation. In such embodiments, the wet laboratory assay used to detect methylation may vary from those described herein. Further, the methylation state vectors discussed herein may contain elements that are generally sites where methylation has or has not occurred (even if those sites are not CpG sites specifically). With that substitution, the remainder of the processes described herein are the same, and consequently the inventive concepts described herein are applicable to those other forms of methylation.

I.B. Definitions

The term "individual" refers to a human individual. The term "healthy individual" refers to an individual presumed or known to not have a cancer or disease. The term "subject" refers to an individual who is known to have, or potentially has, a cancer or disease.

The term "source" refers to an origin of nucleic acid fragments. Sources may be human sources including human tissue types or human cell types. Alternatively sources may be non-human sources such as viruses, bacteria, fetuses, etc.

The term "cell free nucleic acid" or "cfNA" refers to nucleic acid fragments that circulate in an individual's body (e.g., blood) and originate from one or more healthy cells and/or from one or more cancer cells. The term "cell free DNA," or "cfDNA" refers to deoxyribonucleic acid fragments that circulate in an individual's body (e.g., blood). Additionally cfNAs or cfDNA in an individual's body may come from other non-human sources.

The term "genomic nucleic acid," "genomic DNA," or "gDNA" refers to nucleic acid molecules or deoxyribonucleic acid molecules obtained from one or more cells. In various embodiments, gDNA can be extracted from healthy cells (e.g., non-tumor cells) or from tumor cells (e.g., a biopsy sample). In some embodiments, gDNA can be extracted from a cell derived from a blood cell lineage, such as a white blood cell.

The term "circulating tumor DNA" or "ctDNA" refers to nucleic acid fragments that originate from tumor cells or other types of cancer cells, and which may be released into a bodily fluid of an individual (e.g., blood, sweat, urine, or saliva) as result of biological processes such as apoptosis or necrosis of dying cells or actively released by viable tumor cells.

The term "DNA fragment," or "fragment" may generally refer to any portion of deoxyribonucleic acid molecule, i.e., cfDNA, gDNA, ctDNA, etc. For example, a DNA molecule can be broken up, or fragmented into, a plurality of segments, either through natural processes, as is the case with, e.g., cfDNA fragments that can naturally occur within a biological sample, or through in vitro manipulation (e.g., known chemical, mechanical or enzymatic fragmentation methods). In some embodiments, as one of skill in the art would readily appreciate, and as described herein, methylation status at one or more methylation sites (e.g., CpG sites) in a fragment can be determined, or inferred, from one or more sequence reads derived from the fragment. For example, the nucleotide base sequence of a DNA fragment or molecule can be determined from sequence reads derived from the DNA fragment, and thus, methylation status at one or more methylation sites (e.g., CpG sites) in the original fragment determined or inferred. Accordingly, "fragment" and "sequence read" can be used interchangeably herein.

The term "sequence read," "sequence reads," or "reads," used interchangeably herein, refer to a nucleotide sequence produced by any sequencing process described herein or known in the art. Reads can be generated from one end of nucleic acid fragments ("single-end reads"), or generated from both ends of nucleic acid fragments (e.g., paired-end reads, double-end reads). Sequence reads can be obtained through various methods known in the art. As described herein, the nucleotide base sequence of a DNA fragment or molecule can be determined, or inferred, from sequence reads derived from the DNA fragment or molecule, and thus, "fragment" and "sequence read" can be used interchangeably in various embodiments described herein.

The term "sequencing depth" or "depth" refers to a total number of sequence reads or read segments at a given genomic location or loci from a test sample from an individual.

II. Sample Processing

II.A. Generating Methylation State Vectors for DNA Fragments

FIG. 1A is a flowchart describing a process 100 of sequencing a fragment of cell-free (cf) DNA to obtain a methylation state vector, according to an embodiment. In order to analyze DNA methylation, an analytics system first obtains 110 a sample from an individual comprising a plurality of cfDNA molecules. Generally, samples may be from healthy individuals, subjects known to have or suspected of having cancer, or subjects where no prior information is known. The test sample may be a sample selected from the group consisting of blood, plasma, serum, urine, fecal, and saliva samples. Alternatively, the test sample may comprise a sample selected from the group consisting of whole blood, a blood fraction (e.g., white blood cells (WBCs)), a tissue biopsy, pleural fluid, pericardial fluid, cerebral spinal fluid, and peritoneal fluid. In additional embodiments, the process 100 may be applied to sequence other types of DNA molecules.

From the sample, the analytics system isolates each cfDNA molecule. The cfDNA molecules are treated to convert unmethylated cytosines to uracils. In one embodiment, the method uses a bisulfite treatment of the DNA which converts the unmethylated cytosines to uracils without converting the methylated cytosines. For example, a commercial kit such as the EZ DNA Methylation™—Gold, EZ DNA Methylation™—Direct or an EZ DNA Methylation™ —Lightning kit (available from Zymo Research Corp (Irvine, CA)) is used for the bisulfite conversion. In another embodiment, the conversion of unmethylated cytosines to uracils is accomplished using an enzymatic reaction. For example, the conversion can use a commercially available kit for conversion of unmethylated cytosines to uracils, such as APOBEC-Seq (NEBiolabs, Ipswich, MA).

From the converted cfDNA molecules, a sequencing library is prepared 130. Optionally, the sequencing library may be enriched 135 for cfDNA molecules, or genomic regions, that are informative for cancer status using a plurality of hybridization probes. The hybridization probes are short oligonucleotides capable of hybridizing to particularly specified cfDNA molecules, or targeted regions, and enriching for those fragments or regions for subsequent sequencing and analysis. Hybridization probes may be used to perform a targeted, high-depth analysis of a set of specified CpG sites of interest to the researcher. In one embodiment, the hybridization probes are designed to enrich for DNA molecules that have been treated (e.g., using bisulfite) to convert unmethylated cytosines to uracils. Once prepared, the sequencing library or a portion thereof can be sequenced to obtain a plurality of sequence reads. The sequence reads may be in a computer-readable, digital format for processing and interpretation by computer software.

From the sequence reads, the analytics system determines 150 a location and methylation state for each of CpG site based on alignment to a reference genome. The analytics system generates 160 a methylation state vector for each fragment specifying a location of the fragment in the reference genome (e.g., as specified by the position of the first CpG site in each fragment, or another similar metric), a number of CpG sites in the fragment, and the methylation state of each CpG site in the fragment whether methylated (e.g., denoted as M), unmethylated (e.g., denoted as U), or indeterminate (e.g., denoted as I). The methylation state vectors may be stored in temporary or persistent computer memory for later use and processing. Further, the analytics system may remove duplicate reads or duplicate methylation state vectors from a single subject. In an additional embodiment, the analytics system may determine that a certain fragment has one or more CpG sites that have an indeterminate methylation status. The analytics system may decide to exclude such fragments or selectively include such fragments but build a model accounting for such indeterminate methylation statuses.

Figure 1B:
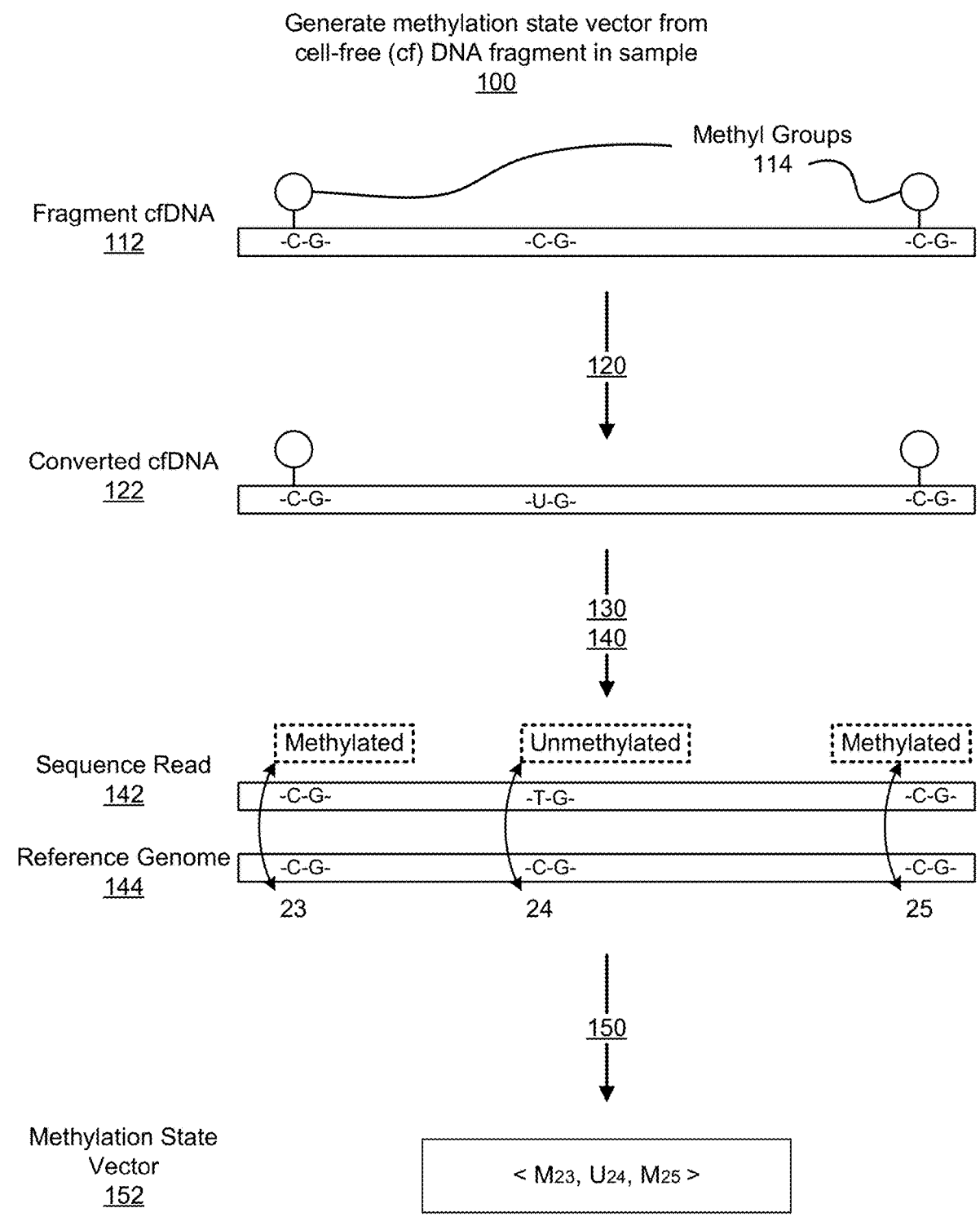
FIG. 1B is an illustration of the process of FIG. 1A of sequencing a fragment of cell-free (cf) DNA to obtain a methylation state vector, according to an embodiment.

FIG. 1B is an illustration of the process 100 of FIG. 1A of sequencing a cfDNA molecule to obtain a methylation state vector, according to an embodiment. As an example, the analytics system receives a cfDNA molecule 112 that, in this example, contains three CpG sites. As shown, the first and third CpG sites of the cfDNA molecule 112 are methylated 114. During the treatment step 120, the cfDNA molecule 112 is converted to generate a converted cfDNA molecule 122. During the treatment 120, the second CpG site which was unmethylated has its cytosine converted to uracil. However, the first and third CpG sites were not converted.

After conversion, a sequencing library 130 is prepared and sequenced 140 generating a sequence read 142. The analytics system aligns 150 the sequence read 142 to a reference genome 144. The reference genome 144 provides the context as to what position in a human genome the fragment cfDNA originates from. In this simplified example, the analytics system aligns 150 the sequence read such that the three CpG sites correlate to CpG sites 23, 24, and 25 (arbitrary reference identifiers used for convenience of description). The analytics system thus generates information both on methylation status of all CpG sites on the cfDNA molecule 112 and the position in the human genome that the CpG sites map to. As shown, the CpG sites on sequence read 142 which were methylated are read as cytosines. In this example, the cytosines appear in the sequence read 142 only in the first and third CpG site which allows one to infer that the first and third CpG sites in the original cfDNA molecule were methylated. Whereas, the second CpG site is read as a thymine (U is converted to T during the sequencing process), and thus, one can infer that the second CpG site was unmethylated in the original cfDNA molecule. With these two pieces of information, the methylation status and location, the analytics system generates 160 a methylation state vector 152 for the fragment cfDNA 112. In this example, the resulting methylation state vector 152 is $<M_{23}, U_{24}, M_{25}>$, wherein M corresponds to a methylated CpG site, U corresponds to an unmethylated CpG site, and the subscript number corresponds to a position of each CpG site in the reference genome.

Figure 1C:
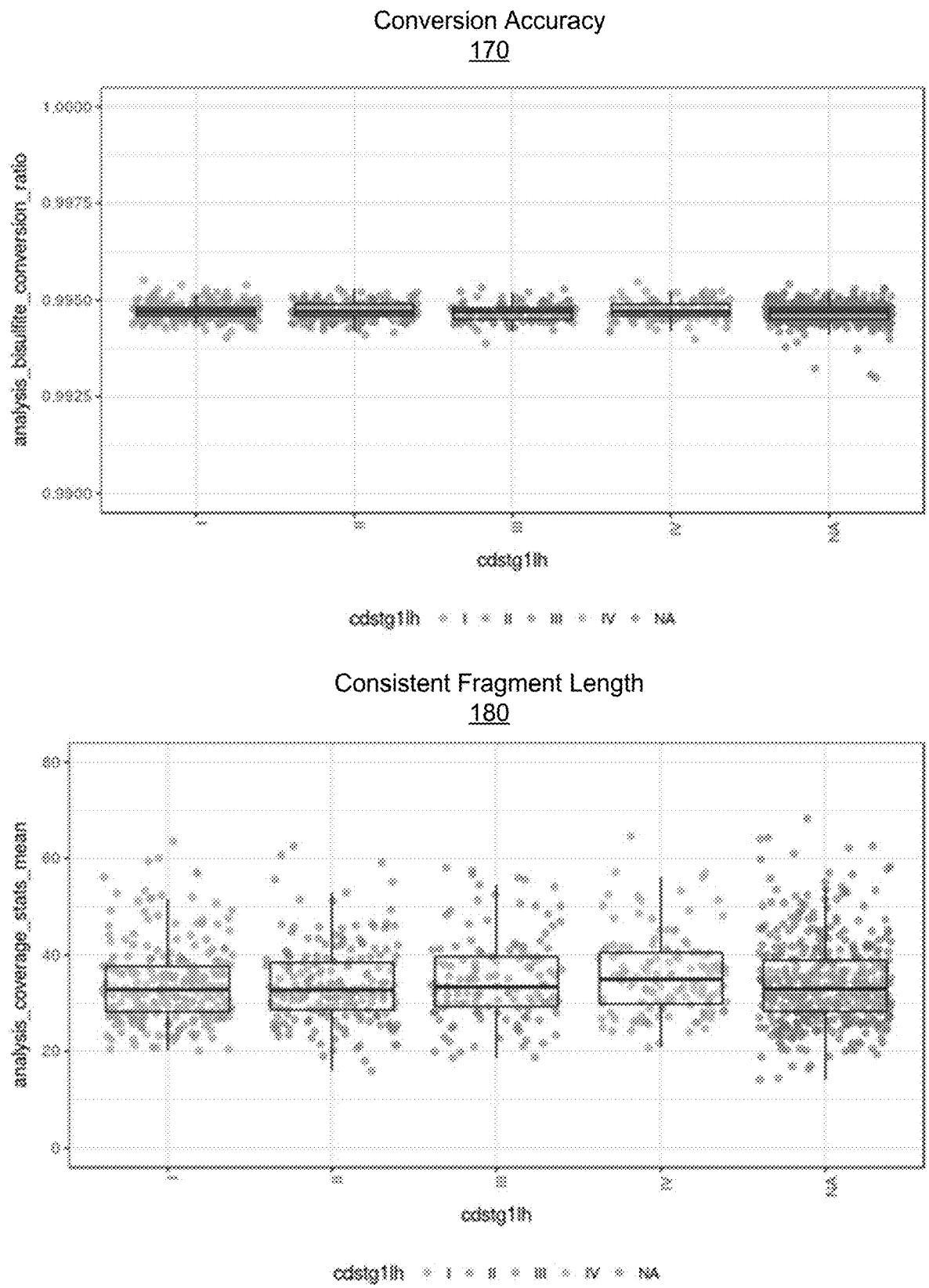
FIGS. 1C & 1D show three graphs of data validating consistency of sequencing from a control group, according to an embodiment.
Figure 1D:
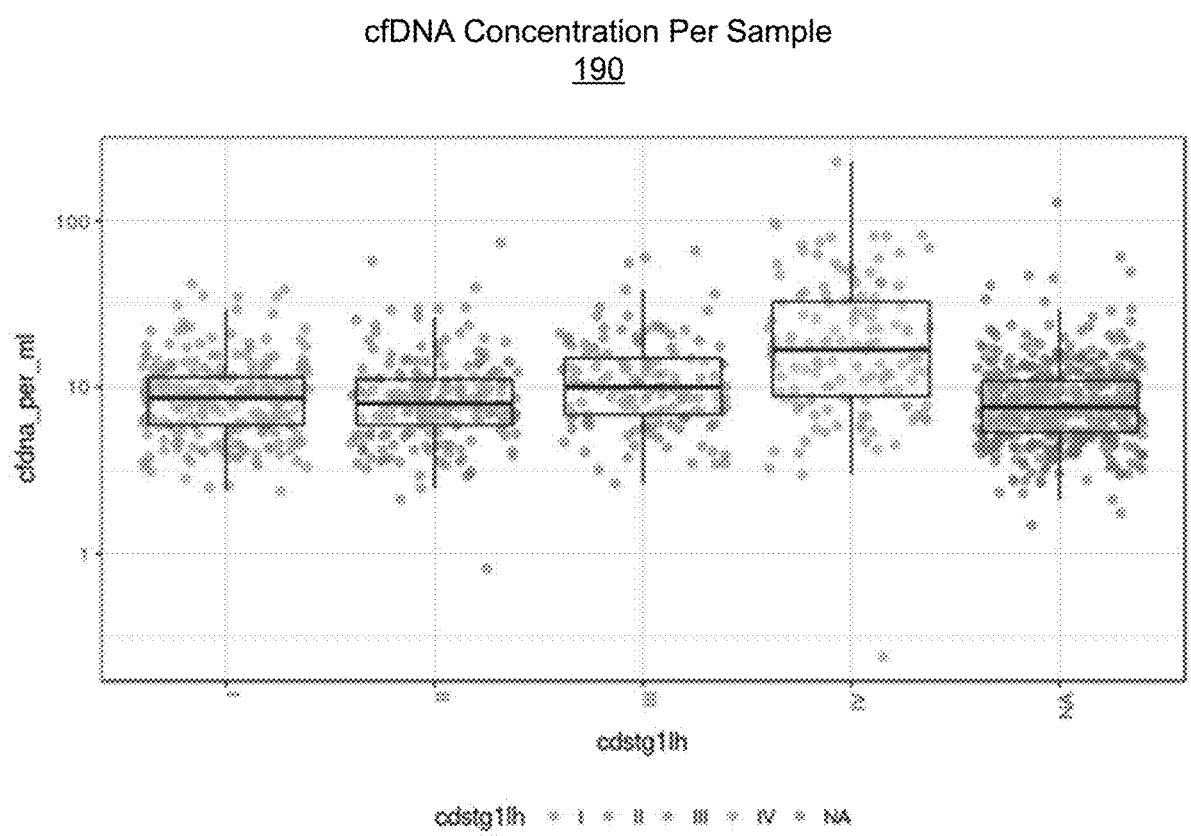

FIGS. 1C & 1D show three graphs of data validating consistency of sequencing from a control group. The first graph 170 shows conversion accuracy of conversion of unmethylated cytosines to uracil (step 120) on cfDNA molecule obtained from a test sample across subjects in varying stages of cancer—stage I, stage II, stage III, stage IV, and non-cancer. As shown, there was uniform consistency in converting unmethylated cytosines on cfDNA molecules into uracils. There was an overall conversion accuracy of 99.47% with a precision at ±0.024%. The second graph 180 shows mean coverage over varying stages of cancer. The mean coverage over all groups being ~34× mean across the genome coverage of DNA molecules, using only those confidently mapped to the genome are counted. The third graph 190 shows concentration of cfDNA per sample across varying stages of cancer.

Although not shown, the analytics system is one or more computing devices configured to receive sequencing data from a sequencer and perform various aspects of processing as described herein. Each computing device can be one of a personal computer (PC), a desktop computer, a laptop computer, a notebook, a tablet PC, a mobile device. A computing device can be communicatively coupled to the sequencer through a wireless, wired, or a combination of wireless and wired communication technologies. Generally, the computing device is configured with a processor and memory storing computer instructions that, when executed by the processor, cause the processor to perform steps as described in the remainder of this description. Generally, the amount of genetic data and data derived therefrom is sufficiently large, and the amount of computational power required so great, so as to be impossible to be performed on paper or by the human mind alone.

II.B. Calculating Sample Vectors for a Sample

FIG. 2A is a flowchart describing a process 200 of calculating sample vectors for a deconvolution model, according to an embodiment. The analytics system generates a set of methylation state vectors from the DNA molecules present in a sample via the process 100 of FIG. 1A; the methylation state vectors each specifying a location of the fragment in the reference genome (e.g., as specified by the position of the first CpG site in each fragment, or another similar metric), a number of CpG sites in the fragment, and the methylation state of each CpG site in the fragment whether methylated (e.g., denoted as M), unmethylated (e.g., denoted as U), or indeterminate (e.g., denoted as I).

The analytics system may remove 210 questionable methylation state vectors from the sample. In some embodiments, the analytics system determines that two or more methylation state vectors obtained via the process 110 of FIG. 1A are duplicative. The analytics system may determine the methylation state vectors to be duplicative if the methylation state vectors both cover at most a number of adjacent CpG sites with equivalent methylation states which is above a threshold number. For example, the analytics system determines two methylation state vectors to be duplicative as they both cover at most the same twenty-five adjacent CpG sites with equivalent methylation states which is over the threshold of ten adjacent CpG sites for declaring duplicates. However, the analytics system may choose not to remove potential duplicates if two methylation state vectors cover at most the same ten adjacent CpG sites but only five adjacent CpG sites of the ten have equivalent methylation states. In these instances, the analytics system may truncate the duplicative methylation state vectors into one methylation state vector. Continuing with the example, the analytics system combines the two methylation state vectors to at least include the shared twenty-five adjacent CpG sites with equivalent methylation states, but may also include additional CpG sites from either of the methylation state vectors that are not included in the other methylation state vector.

In other embodiments, the analytics system may apply one or more other filters to remove 210 questionable methylation state vectors from the sample. One such filter identifies fragments that were not properly converted. This filter evaluates whether a very high percentage (e.g., any percentage in the range of 95% to 100%) of cytosines on a fragment remain unconverted (e.g., considering cytosines not in CpG sites or considering all cytosines on fragment) which would indicate methylation of a high percentage of cytosines outside of CpG sites. Methylation of cytosines outside of CpG sites are rarities indicating an extreme unlikelihood that high percentage of these cytosines outside of CpG sites would be methylated.

For each CpG site [n] under consideration, the analytics system identifies 220 methylation state vectors inclusive of that CpG site [n]. Of the identified methylation state vectors inclusive of that CpG site [n], the analytics system calculates 230 a methylation metric $[\beta_{n,\ sample}]$ corresponding to a percentage of the CpG sites in those vectors that are methylated. For example, one hundred of five hundred methylation state vectors identified inclusive of a CpG site [5] are methylated such that the aggregate percentage of methylation is 20%. The methylation metric at that site for the sample $[\beta_{5,\ sample}]$ may then be 0.2 or 20%. In alternative embodiments, the analytics system may incorporate a damping factor to the calculation of the methylation metric, e.g., for samples with lower coverage, wherein the damping factor may depend on the coverage. As an example, the methylation metric inclusive of the damping factor may be defined as a fraction with a numerator equaling the number of methylation vectors with the CpG site methylated added with a damping variable and a denominator equaling the total number of methylation vectors covering that CpG site added with twice the damping variable. In other embodiments, the methylation metric $[\beta_{n,\ sample}]$ may be determined otherwise. The analytics system generates 240 a sample vector $[\beta_{N,\ sample}]$ inclusive of methylation metrics $[\beta_{n,\ sample}]$ over the set of CpG sites [N] under consideration. In some embodiments, the number of CpG sites [N] in consideration may vary, e.g., all CpG sites in entire genome, subset of CpG sites in entire genome, all CpG sites in one section of the genome, etc.

In some embodiments, the methylation metric $[\beta_{n,\ sample}]$ may incorporate fragment level information (e.g., fraction of fragments overlapping the CpG site that are hypermethylated or hypomethylated). The analytics system utilizes a set of anomalously methylated fragments to compute the methylation metrics. Fragments of a sample may be determined to be anomalously methylated according to principles described further in Section II.C. Identifying Anomalous Fragments. The analytics system identifies, at step 220, methylation state vectors from anomalously methylated fragments inclusive of a CpG site [n]. The analytics system calculates a percentage of methylation among the anomalously methylated fragments as the methylation metric $[\beta_{n,\ sample}]$. Further, this application incorporates the entirety of International Application No. PCT/AU2013/001088, filed Sep. 20, 2013, entitled "Non-Invasive Determination of Methylome of Fetus or Tumor from Plasma", and published as International Publication No. WO 2014/043763.

II.C. Identifying Anomalous Fragments

II.C.i. P-Value Filtering

In one embodiment, the analytics system calculates a p-value score for each methylation state vector compared to methylation state vectors from fragments in a healthy control group. The p-value score describes a probability of observing the methylation status matching that methylation state vector or other methylation state vectors even less probable in the healthy control group. In order to determine a DNA fragment to be anomalously methylated, the analytics system uses a healthy control group with a majority of fragments that are normally methylated. When conducting this probabilistic analysis for determining anomalous fragments, the determination holds weight in comparison with the group of control subjects that make up the healthy control group. To ensure robustness in the healthy control group, the analytics system may select some threshold number of healthy individuals to source samples including DNA fragments. FIG. 2B below describes the method of generating a data structure for a healthy control group with which the analytics system may calculate p-value scores.

Figure 2C:
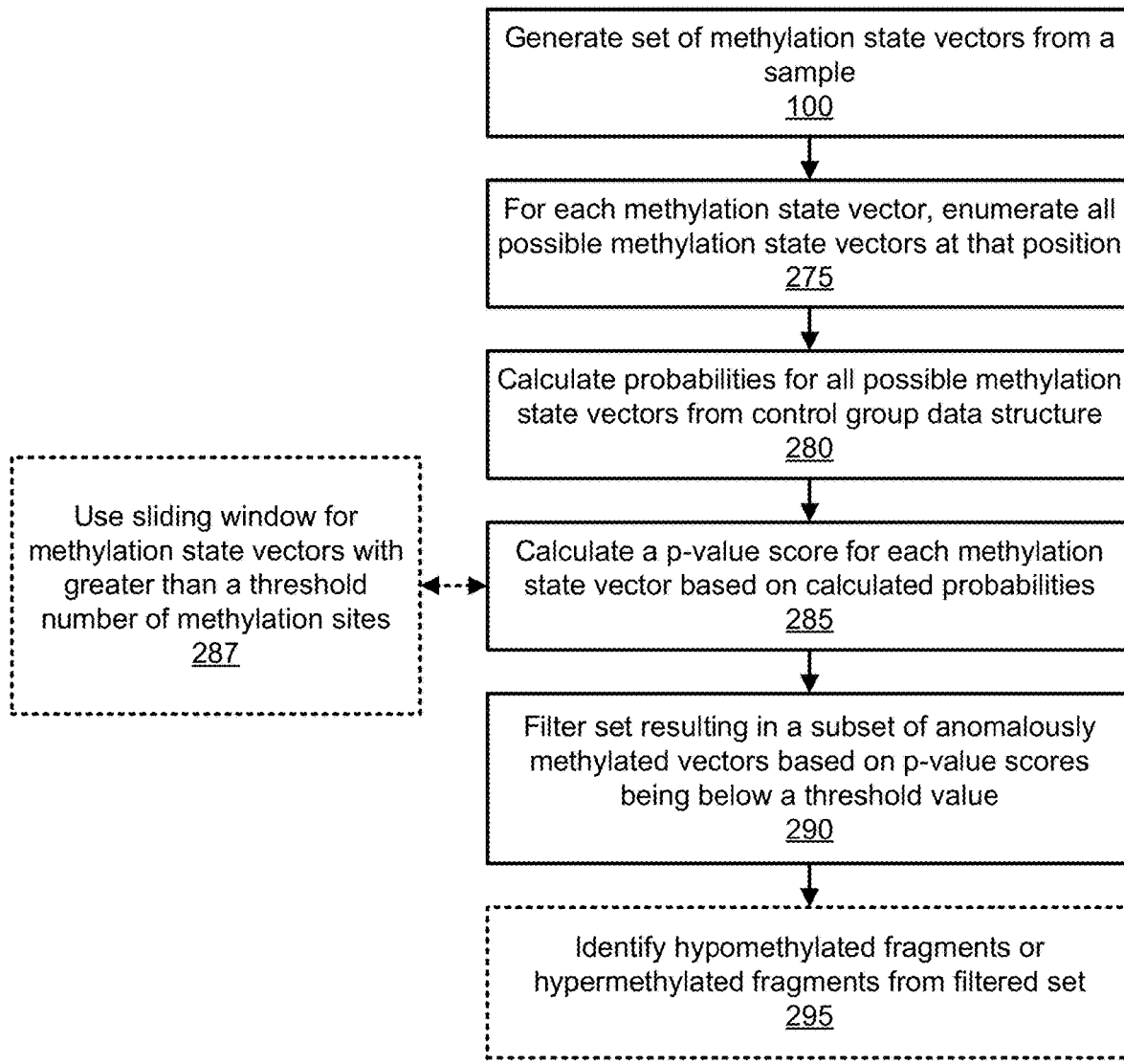
FIG. 2C is a flowchart describing a process for identifying anomalously methylated fragments from an individual, according to an embodiment.

FIG. 2C describes the method of calculating a p-value score with the generated data structure.

FIG. 2B is a flowchart describing a process 250 of generating a data structure for a healthy control group, according to an embodiment. To create a healthy control group data structure, the analytics system receives a plurality of DNA fragments (e.g., cfDNA) from a plurality of healthy individuals. A methylation state vector is identified for each fragment, for example via the process 100.

With each fragment's methylation state vector, the analytics system subdivides 205 the methylation state vector into strings of CpG sites. In one embodiment, the analytics system subdivides 255 the methylation state vector such that the resulting strings are all less than a given length. For example, a methylation state vector of length 11 may be subdivided into strings of length less than or equal to 3 would result in 9 strings of length 3, 10 strings of length 2, and 11 strings of length 1. In another example, a methylation state vector of length 7 being subdivided into strings of length less than or equal to 4 would result in 4 strings of length 4, 5 strings of length 3, 6 strings of length 2, and 7 strings of length 1. If a methylation state vector is shorter than or the same length as the specified string length, then the methylation state vector may be converted into a single string containing all of the CpG sites of the vector.

The analytics system tallies 260 the strings by counting, for each possible CpG site and possibility of methylation states in the vector, the number of strings present in the control group having the specified CpG site as the first CpG site in the string and having that possibility of methylation states. For example, at a given CpG site and considering string lengths of 3, there are 2^3 or 8 possible string configurations. At that given CpG site, for each of the 8 possible string configurations, the analytics system tallies 260 how many occurrences of each methylation state vector possibility come up in the control group. Continuing this example, this may involve tallying the following quantities: $<M_x, M_{x+1}, M_{x+2}>, <M_x, M_{x+1}, U_{x+2}>, \ldots, <U_x, U_{x+1}, U_{x+2}>$ for each starting CpG site x in the reference genome. The analytics system creates 265 the data structure storing the tallied counts for each starting CpG site and string possibility.

There are several benefits to setting an upper limit on string length. First, depending on the maximum length for a string, the size of the data structure created by the analytics system can dramatically increase in size. For instance, maximum string length of 4 means that every CpG site has at the very least 2^4 numbers to tally for strings of length 4. Increasing the maximum string length to 5 means that every CpG site has an additional 2^4 or 16 numbers to tally, doubling the numbers to tally (and computer memory required) compared to the prior string length. Reducing string size helps keep the data structure creation and performance (e.g., use for later accessing as described below), in terms of computational and storage, reasonable. Second, a statistical consideration to limiting the maximum string length is to avoid overfitting downstream models that use the string counts. If long strings of CpG sites do not, biologically, have a strong effect on the outcome (e.g., predictions of anomalousness that predictive of the presence of cancer), calculating probabilities based on large strings of CpG sites can be problematic as it requires a significant amount of data that may not be available, and thus would be too sparse for a model to perform appropriately. For example, calculating a probability of anomalousness/cancer conditioned on the prior 100 CpG sites would require counts of strings in the data structure of length 100, ideally some matching exactly the prior 100 methylation states. If only sparse counts of strings of length 100 are available, there will be insufficient data to determine whether a given string of length of 100 in a test sample is anomalous or not.

FIG. 2C is a flowchart describing a process 270 for identifying anomalously methylated fragments from an individual, according to an embodiment. In process 270, the analytics system generates 100 methylation state vectors from cfDNA fragments of the subject. The analytics system handles each methylation state vector as follows.

For a given methylation state vector, the analytics system enumerates 275 all possibilities of methylation state vectors having the same starting CpG site and same length (i.e., set of CpG sites) in the methylation state vector. As each methylation state is generally either methylated or unmethylated there are effectively two possible states at each CpG site, and thus the count of distinct possibilities of methylation state vectors depends on a power of 2, such that a methylation state vector of length n would be associated with $2^n$ possibilities of methylation state vectors. With methylation state vectors inclusive of indeterminate states for one or more CpG sites, the analytics system may enumerate 275 possibilities of methylation state vectors considering only CpG sites that have observed states.

The analytics system calculates 280 the probability of observing each possibility of methylation state vector for the identified starting CpG site and methylation state vector length by accessing the healthy control group data structure. In one embodiment, calculating the probability of observing a given possibility uses a Markov chain probability to model the joint probability calculation. In other embodiments, calculation methods other than Markov chain probabilities are used to determine the probability of observing each possibility of methylation state vector.

The analytics system calculates 285 a p-value score for the methylation state vector using the calculated probabilities for each possibility. In one embodiment, this includes identifying the calculated probability corresponding to the possibility that matches the methylation state vector in question. Specifically, this is the possibility having the same set of CpG sites, or similarly the same starting CpG site and length as the methylation state vector. The analytics system sums the calculated probabilities of any possibilities having probabilities less than or equal to the identified probability to generate the p-value score.

This p-value represents the probability of observing the methylation state vector of the fragment or other methylation state vectors even less probable in the healthy control group. A low p-value score, thereby, generally corresponds to a methylation state vector which is rare in a healthy individual, and which causes the fragment to be labeled anomalously methylated, relative to the healthy control group. A high p-value score generally relates to a methylation state vector is expected to be present, in a relative sense, in a healthy individual. If the healthy control group is a non-cancerous group, for example, a low p-value indicates that the fragment is anomalous methylated relative to the non-cancer group, and therefore possibly indicative of the presence of cancer in the test subject.

As above, the analytics system calculates p-value scores for each of a plurality of methylation state vectors, each representing a cfDNA fragment in the test sample. To identify which of the fragments are anomalously methylated, the analytics system may filter 290 the set of methylation state vectors based on their p-value scores. In one embodiment, filtering is performed by comparing the p-values scores against a threshold and keeping only those fragments below the threshold. This threshold p-value score could be on the order of 0.1, 0.01, 0.001, 0.0001, or similar.

According to example results from the process 270, the analytics system yields a median (range) of 2,800 (1,500-12,000) fragments with anomalous methylation patterns for participants without cancer in training, and a median (range) of 3,000 (1,200-220,000) fragments with anomalous methylation patterns for participants with cancer in training. These filtered sets of fragments with anomalous methylation patterns may be used for the downstream analyses as described below in Section III.

In one embodiment, the analytics system uses 287 a sliding window to determine possibilities of methylation state vectors and calculate p-values. Rather than enumerating possibilities and calculating p-values for entire methylation state vectors, the analytics system enumerates possibilities and calculates p-values for only a window of sequential CpG sites, where the window is shorter in length (of CpG sites) than at least some fragments (otherwise, the window would serve no purpose). The window length may be static, user determined, dynamic, or otherwise selected.

In calculating p-values for a methylation state vector larger than the window, the window identifies the sequential set of CpG sites from the vector within the window starting from the first CpG site in the vector. The analytic system calculates a p-value score for the window including the first CpG site. The analytics system then "slides" the window to the second CpG site in the vector, and calculates another p-value score for the second window. Thus, for a window size l and methylation vector length m, each methylation state vector will generate m−l+1 p-value scores. After completing the p-value calculations for each portion of the vector, the lowest p-value score from all sliding windows is taken as the overall p-value score for the methylation state vector. In another embodiment, the analytics system aggregates the p-value scores for the methylation state vectors to generate an overall p-value score.

Using the sliding window helps to reduce the number of enumerated possibilities of methylation state vectors and their corresponding probability calculations that would otherwise need to be performed. To give a realistic example, it is possible for fragments to have upwards of 54 CpG sites. Instead of computing probabilities for $2^{54}$ (~$1.8 \times 10^{16}$) possibilities to generate a single p-score, the analytics system can instead use a window of size 5 (for example) which results in 50 p-value calculations for each of the 50 windows of the methylation state vector for that fragment. Each of the 50 calculations enumerates $2^5$ (32) possibilities of methylation state vectors, which total results in $50 \times 2^5$ ($1.6 \times 10^3$) probability calculations. This results in a vast reduction of calculations to be performed, with no meaningful hit to the accurate identification of anomalous fragments.

In embodiments with indeterminate states, the analytics system may calculate a p-value score summing out CpG sites with indeterminates states in a fragment's methylation state vector. The analytics system identifies all possibilities that have consensus with the all methylation states of the methylation state vector excluding the indeterminate states. The analytics system may assign the probability to the methylation state vector as a sum of the probabilities of the identified possibilities. As an example, the analytics system calculates a probability of a methylation state vector of <$M_1$, $I_2$, $U_3$> as a sum of the probabilities for the possibilities of methylation state vectors of <$M_1$, $M_2$, $U_3$> and <$M_1$, $U_2$, $U_3$> since methylation states for CpG sites 1 and 3 are observed and in consensus with the fragment's methylation states at CpG sites 1 and 3. This method of summing out CpG sites with indeterminate states uses calculations of probabilities of possibilities up to $2^i$, wherein i denotes the number of indeterminate states in the methylation state vector. In additional embodiments, a dynamic programming algorithm may be implemented to calculate the probability of a methylation state vector with one or more indeterminate states. Advantageously, the dynamic programming algorithm operates in linear computational time.

In one embodiment, the computational burden of calculating probabilities and/or p-value scores may be further reduced by caching at least some calculations. For example, the analytic system may cache in transitory or persistent memory calculations of probabilities for possibilities of methylation state vectors (or windows thereof). If other fragments have the same CpG sites, caching the possibility probabilities allows for efficient calculation of p-score values without needing to re-calculate the underlying possibility probabilities. Equivalently, the analytics system may calculate p-value scores for each of the possibilities of methylation state vectors associated with a set of CpG sites from vector (or window thereof). The analytics system may cache the p-value scores for use in determining the p-value scores of other fragments including the same CpG sites. Generally, the p-value scores of possibilities of methylation state vectors having the same CpG sites may be used to determine the p-value score of a different one of the possibilities from the same set of CpG sites.

II.C.ii. Hypermethylated Fragments and Hypomethylated Fragments

In another embodiment, the analytics system determines anomalous fragments as fragments with over a threshold number of CpG sites and either with over a threshold percentage of the CpG sites methylated or with over a threshold percentage of CpG sites unmethylated; the analytics system identifies 295 such fragments as hypermethylated fragments or hypomethylated fragments. Example thresholds for length of fragments (or CpG sites) include more than 3, 4, 5, 6, 7, 8, 9, 10, etc. Example percentage thresholds of methylation or unmethylation include more than 80%, 85%, 90%, or 95%, or any other percentage within the range of 50%-100%.

II.D. Example Analytics System

Figure 5A:
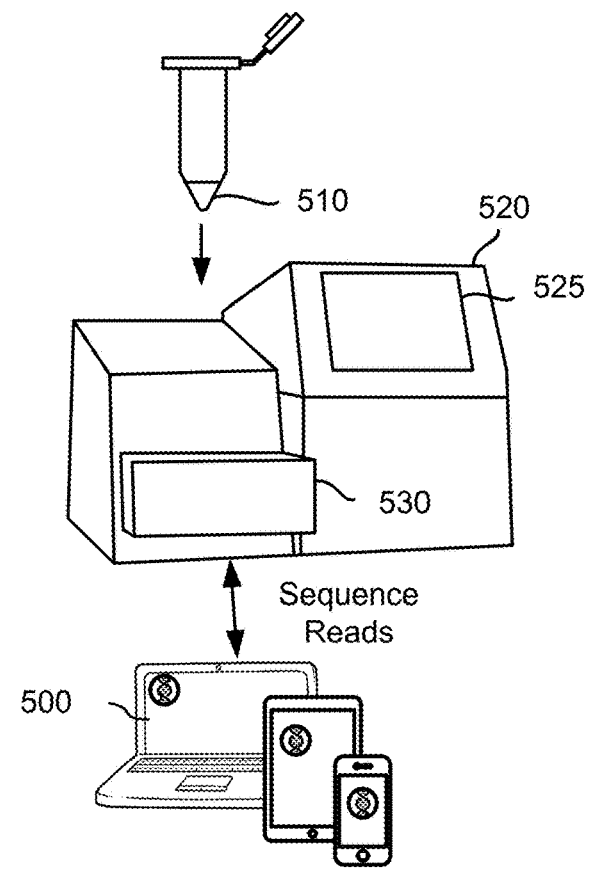
FIG. 5A illustrates a flowchart of devices for sequencing nucleic acid samples according to one embodiment.

FIG. 5A illustrates communication flow between devices for sequencing nucleic acid samples according to one embodiment. This illustrative flowchart includes devices such as a sequencer 520 and an analytics system 500. The sequencer 520 and the analytics system 500 may work in tandem to perform one or more steps in the process 100 of FIG. 1A.

In various embodiments, the sequencer 520 receives an enriched nucleic acid sample 510. As shown in FIG. 5A, the sequencer 520 can include a graphical user interface 525 that enables user interactions with particular tasks (e.g., initiate sequencing or terminate sequencing) as well as one more loading stations 530 for loading a sequencing cartridge including the enriched fragment samples and/or for loading necessary buffers for performing the sequencing assays. Therefore, once a user of the sequencer 520 has provided the necessary reagents and sequencing cartridge teto the loading stations 530 of the sequencer 520, the user can initiate sequencing by interacting with the graphical user interface 525 of the sequencer 520. Once initiated, the sequencer 520 performs the sequencing and outputs the sequence reads of the enriched fragments from the nucleic acid sample 510.

In some embodiments, the sequencer 520 is communicatively coupled with the analytics system 500. The analytics system 500 includes some number of computing devices used for processing the sequence reads for various applications such as assessing methylation status at one or more CpG sites, variant calling or quality control. The sequencer 520 may provide the sequence reads in a BAM file format to the analytics system 500. The analytics system 500 can be communicatively coupled to the sequencer 520 through a wireless, wired, or a combination of wireless and wired communication technologies. Generally, the analytics system 500 is configured with a processor and non-transitory computer-readable storage medium storing computer instructions that, when executed by the processor, cause the processor to process the sequence reads or to perform one or more steps of any of the methods or processes disclosed herein.

In some embodiments, the sequence reads may be aligned to a reference genome using known methods in the art to determine alignment position information, e.g., via step 140 of the process 100 in FIG. 1A. Alignment position may generally describe a beginning position and an end position of a region in the reference genome that corresponds to a beginning nucleotide based and an end nucleotide base of a given sequence read. Corresponding to methylation sequencing, the alignment position information may be generalized to indicate a first CpG site and a last CpG site included in the sequence read according to the alignment to the reference genome. The alignment position information may further indicate methylation statuses and locations of all CpG sites in a given sequence read. A region in the reference genome may be associated with a gene or a segment of a gene; as such, the analytics system 500 may label a sequence read with one or more genes that align to the sequence read. In one embodiment, fragment length (or size) is be determined from the beginning and end positions.

In various embodiments, for example when a paired-end sequencing process is used, a sequence read is comprised of a read pair denoted as R_1 and R_2. For example, the first read R_1 may be sequenced from a first end of a double-stranded DNA (dsDNA) molecule whereas the second read R_2 may be sequenced from the second end of the double-stranded DNA (dsDNA). Therefore, nucleotide base pairs of the first read R_1 and second read R_2 may be aligned consistently (e.g., in opposite orientations) with nucleotide bases of the reference genome. Alignment position information derived from the read pair R_1 and R_2 may include a beginning position in the reference genome that corresponds to an end of a first read (e.g., R_1) and an end position in the reference genome that corresponds to an end of a second read (e.g., R_2). In other words, the beginning position and end position in the reference genome represent the likely location within the reference genome to which the nucleic acid fragment corresponds. An output file having SAM (sequence alignment map) format or BAM (binary) format may be generated and output for further analysis.

Figure 5B:
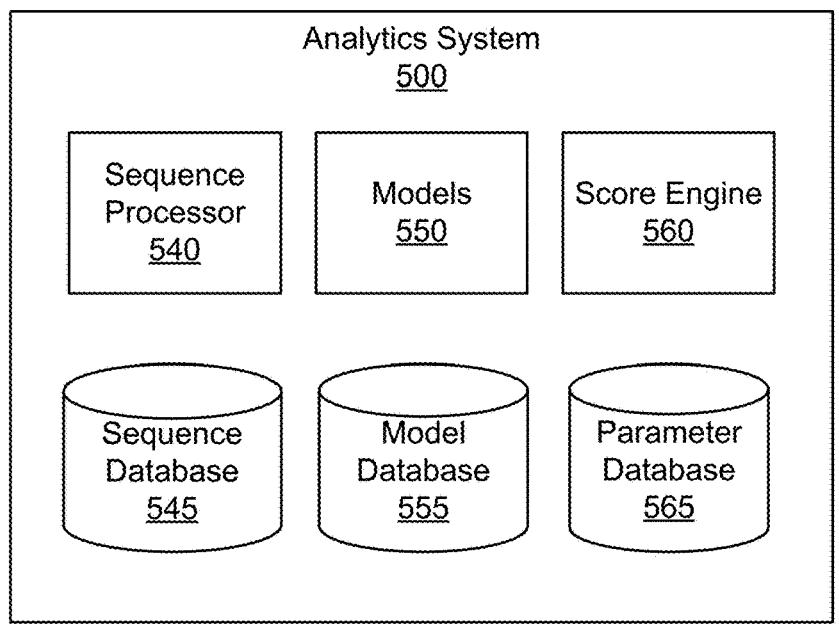
FIG. 5B is a block diagram of an analytics system, according to an embodiment.

Referring now to FIG. 5B, FIG. 5B is block diagram of an analytics system 500 for processing DNA samples according to one embodiment. The analytics system implements one or more computing devices for use in analyzing DNA samples. The analytics system 500 includes a sequence processor 540, sequence database 545, models 550, model database 555, score engine 560, and parameter database 565. In some embodiments, the analytics system 500 performs some or all of the processes 100 of FIG. 1A and 200 of FIG. 2.

The sequence processor 540 generates methylation state vectors for fragments from a sample. At each CpG site on a fragment, the sequence processor 540 generates a methylation state vector for each fragment specifying a location of the fragment in the reference genome, a number of CpG sites in the fragment, and the methylation state of each CpG site in the fragment whether methylated, unmethylated, or indeterminate via the process 100 of FIG. 1A. The sequence processor 540 may store methylation state vectors for fragments in the sequence database 545. Data in the sequence database 545 may be organized such that the methylation state vectors from a sample are associated to one another.

Further, multiple different models 550 may be stored in the model database 555 or retrieved for use with test samples. For example, one model is a trained deconvolution model for determining source of origin predictions for a test sample with many fragments from a variety of sources. The training and use of the deconvolution model will be further discussed in conjunction with Section III. Deconvolution Model for Determining Source of Origin Prediction. In another example, another model is a trained cancer classifier for determining a cancer prediction for a test sample using a feature vector derived from a source of origin prediction. The training and use of the trained cancer classifier will be further discussed in conjunction with Section IV. Cancer Classifier for Determining Cancer. The analytics system 500 may train the one or more models 550 and store various trained parameters in the parameter database 565. The analytics system 500 stores the models 550 along with relevant metric formulae and functions in the model database 555.

During inference with the models 550, the score engine 560 uses the one or more models to return outputs. The score engine 560 accesses the models 550 in the model database 555, such as a cancer prediction model, along with retrieving trained parameters from the parameter database 565, such as anomalous fragments derived from training fragments. The score engine 560 applies an accessed model to data representative of anomalous fragments within a test sample, and the model produces an output representative of a likelihood that the test sample is associated with a disease state based on the data representative of the anomalous fragments. As noted herein, the disease state can be a presence or absence of cancer generally, a presence or absence of a particular type of cancer, or a presence or absence of a non-cancer disease or human condition. In some use cases, the score engine 560 further calculates metrics correlating to a confidence in the outputs produced by the accessed model. In other use cases, the score engine 560 calculates other intermediary values for use in the model.

III. Deconvolution Model for Determining Source of Origin Prediction

III.A. Training of Deconvolution Model

Figure 3C:
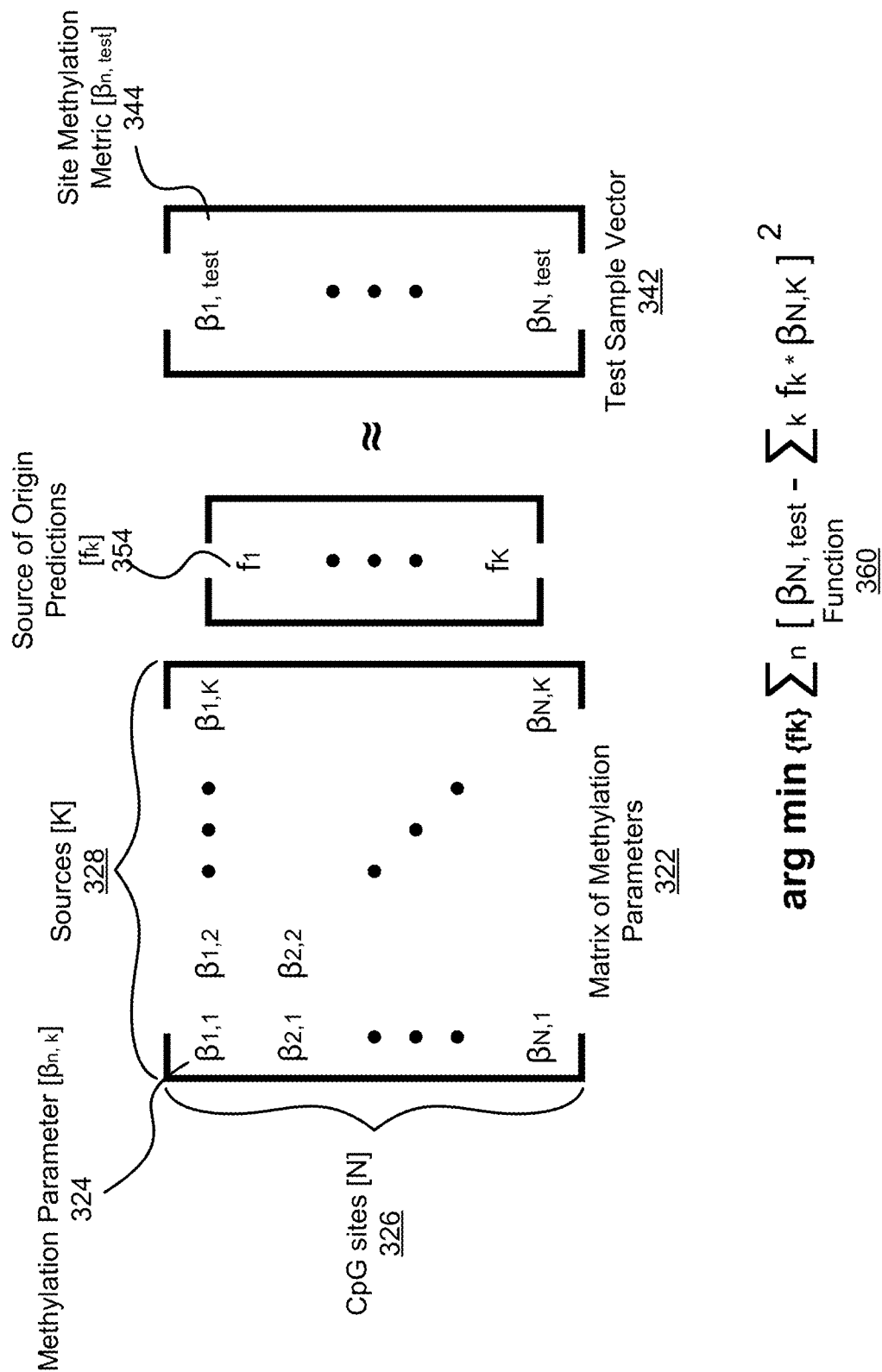
FIG. 3C is an illustration of the process of FIG. 3B of generating a source of origin prediction using a deconvolution model, according to an embodiment.

FIG. 3A is a flowchart describing a process 300 of training a deconvolution model, according to an embodiment. The deconvolution model is used to determine a source of origin prediction for a test sample. The analytics system first obtains 305 a set of training samples, each originating from one known source [k] from among a number of known sources [K]. The obtaining 305 process includes determining a training sample vector $[\beta_{N,\ training}]$ for each of the training samples. In one embodiment, this is carried out according to the process 200 of FIG. 2. FIG. 3C is an illustration of the deconvolution model including the notation used in the following description. FIG. 3C will be referenced throughout the remaining description of the deconvolution model.

The training samples originate from individuals. The various tissue types may include any combination of a large intestine tissue type, a breast tissue type, a thyroid tissue type, a lung tissue type, a bladder tissue type, a cervix tissue type, a colorectal tissue type, an esophagus tissue type, a gastric tissue type, a tonsil tissue type, a liver tissue type, a white blood cell tissue type, an ovary tissue type, a pancreas tissue type, a prostate tissue type, a kidney tissue type, and a uterus tissue type. The cell types may include any combination of a B cell type, a dendritic cell type, an endothelial cell type, an eosinophil cell type, an erythroblast cell type, a macrophage cell type, a megakaryocyte cell type, a monocyte cell type, a natural killer cell type, a neutrophil cell type, a precursor B cell type, a T cell type, a thymocyte cell type, an adipocyte cell type, a hepatocyte cell type, an islet cell type, and a preadipocyte cell type. The sources [K] considered in the deconvolution model may include any combination of the various tissue types listed and the various cell types listed, and any other tissue type or cell type.

The analytics system generates 310, for each source [k] at each CpG site [n] of a plurality of CpG sites [N], a methylation parameter $[\beta_{n, k}]$ based on the training sample vectors $[\beta_{N, training}]$ for training samples of that source [k]. In one embodiment, the methylation parameter $[\beta_{n, k}]$ is an average of the methylation metric $[\beta_{n, training}]$ over all training sample vectors $[\beta_{N, training}]$ from the source [k]. As a representative example, the analytics system averages a first methylation metric of 0.2 from a first training sample vector at CpG site [n] with a second methylation metric of 0.3 from a second training sample vector at CpG site [n] to define a methylation parameter of 0.25 for the CpG site [n] and the source [k] from which both training sample vectors originate. Referring to FIG. 3C, the analytics system accumulates the methylation parameters $[\beta_{N, K}]$ over the CpG sites [N] 326 for the sources [K] 328 arranged in the matrix of methylation parameters 324.

The analytics system may calculate 315 an information gain for the CpG sites [n] based on the methylation parameters $[\beta_{N, K}]$. In one embodiment, the analytics system calculates an ability to distinguish between pairs of cancer types. For each pair of sources (e.g. liver vs breast), the analytics system calculates how the methylation status at each CpG site can distinguish between the two sources, i.e., calculating mutual information between the pair of sources. The analytics system may rank according to this calculated mutual information for each pair of sources. In one embodiment, the analytics system calculates a standard deviation of methylation parameters for a CpG site $[\beta_{n, K}]$ between the different sources [K]. The calculated standard deviation may be used as information gain, wherein a CpG site [n] with a greater standard deviation corresponds to a set of methylation parameters for that CpG site $[\beta_{n, K}]$ that are more spread out compared to another CpG site with a lower standard deviation. In another embodiment, the analytics system calculates a range of methylation parameters for a CpG site $[\beta_{n, K}]$ by taking a differential between the highest methylation parameter and the lowest methylation parameter across the sources [K]. The greater the standard deviation/spread in methylation parameters, the more distinctly informative a given CpG site is for use in identifying that a subset or one of the sources [k] is the origin of methylation fragments overlapping that CpG site. Consequently, the more useful the CpG site would be if included in the deconvolution model. The inverse is true if the standard deviation is smaller or the spread in maximum to minimum methylation parameters is smaller. In another embodiment, the analytics system uses a combination of the metrics described above in computing the information gain.

According to the calculated information gain from step 315, the analytics system selects 320 a subset of CpG sites [N'] of the CpG sites [N] for use in the deconvolution model based on the information gain. In one embodiment, the analytics system ranks the CpG sites according to the information gain and may then select from the ranking the subset of CpG sites [N'] that have the highest calculated information gain. The methylation parameters $[\beta_{N', K}]$ of the selected CpG sites [N] are kept for use in the deconvolution model. In other embodiments, the analytics system determines a scaling factor for each of the CpG sites [N] based on the calculated information gain. The scaling factors may affect the influence of those CpG sites in the deconvolution model when determining source of origin predictions. For convenience of description, the remainder of the specification refers to set of CpG sites [N] rather than referring to the subset [N'], however in practice wherever the set [N] is used, the subset [N'] could be used instead.

III.B. Use of Deconvolution Model

FIG. 3B is a flowchart describing a process 330 of generating a source of origin prediction using a deconvolution model, according to an embodiment. The analytics system obtains 335 a test sample with DNA molecules of unknown contributions from an unknown set of sources. The test sample vector 342, as shown in FIG. 3C, includes methylation metrics 344 for the CpG sites [N] in consideration. The test sample vector may be determined by any combination of the processes 100 of FIG. 1A and 200 of FIG. 2. In some instances, the test sample vector may have no methylation state vectors that overlap a given CpG site [n] under consideration. In this case, the analytics system may remove consideration of such a CpG site without a methylation state vector overlapping the given CpG site. In some instances, the test sample vector may have methylation metrics that are not present in the set of CpG sites [N] under consideration. In this case, the analytics system may truncate the test sample vector to include methylation metrics for just the CpG sites [N]. The resulting test sample vector $[\beta_{N, test}]$ has a same number of methylation metrics [N] as CpG sites [N].

The analytics system inputs 340 the test sample vector $[\beta_{N, test}]$, methylation parameters $[\beta_{N, K}]$, and a function into the deconvolution model to determine 350 a source of origin prediction $[f_K]$ 354 as shown in FIG. 3C. The function 360 may be the example function shown in FIG. 3C, or another function. Each source prediction describes a likelihood that at least some of the methylation state vectors that make up the test sample vector originated from a given source [k]. In one embodiment, the function minimizes a metric between the test sample vector $[\beta_{N, test}]$ and a matrix product of the methylation parameters $[\beta_{N, K}]$ and a source of origin prediction $[f_K]$.

In one embodiment of steps 345, the analytics system determines the source of origin predictions 354 as follows. The analytics system initializes a randomized source of origin prediction $[f_K]$. The analytics system computes the error according to the metric discussed. The analytics system may then compare the metric to a metric threshold in order for the source of origin prediction to be considered a sufficiently accurate source of origin prediction. If the metric is above the metric threshold, the analytics system may iterate changes in the source of origin prediction $[f_K]$ to decrease the metric. In one example the function 360 employs a steepest descent method for minimizing a metric defined as a L2-norm of the test sample vector $[\beta_{N, test}]$ and a matrix product of the matrix of methylation parameters $[\beta_{N, K}]$ and the source of origin prediction $[f_K]$, the function calculates a gradient of the metric. The function subtracts the gradient of the current iteration of the source of origin prediction from the current iteration of the source of origin prediction to determine a new iteration. Every iteration, the analytics system recalculates the metric and compares against the metric threshold. At any iteration if the metric is below the metric threshold, the analytics system may deem the resulting source of origin prediction as sufficiently accurate. In the example above with steepest descent, the analytics system may define a metric as a L2-norm between two subsequent iterations. In other examples, the analytics system defines the metric as another regularized norm. When the differential between two subsequent iterations is below the metric threshold, the analytics system determines that the final iteration is sufficiently accurate. In some examples, the function may employ other minimization methods, e.g., Newton's method, interior point method, Quasi-Newton method, active set method, etc.

In some additional embodiments, the analytics system imposes conditions on the deconvolution model. In one embodiment, the analytics system imposes a condition that all source predictions need to be greater than or equal to zero. In another embodiment, the analytics system imposes a condition that all source predictions in a source of origin prediction must sum to one or within a tolerance of one.

III.C. Example Results of the Deconvolution Model

Figure 3D:
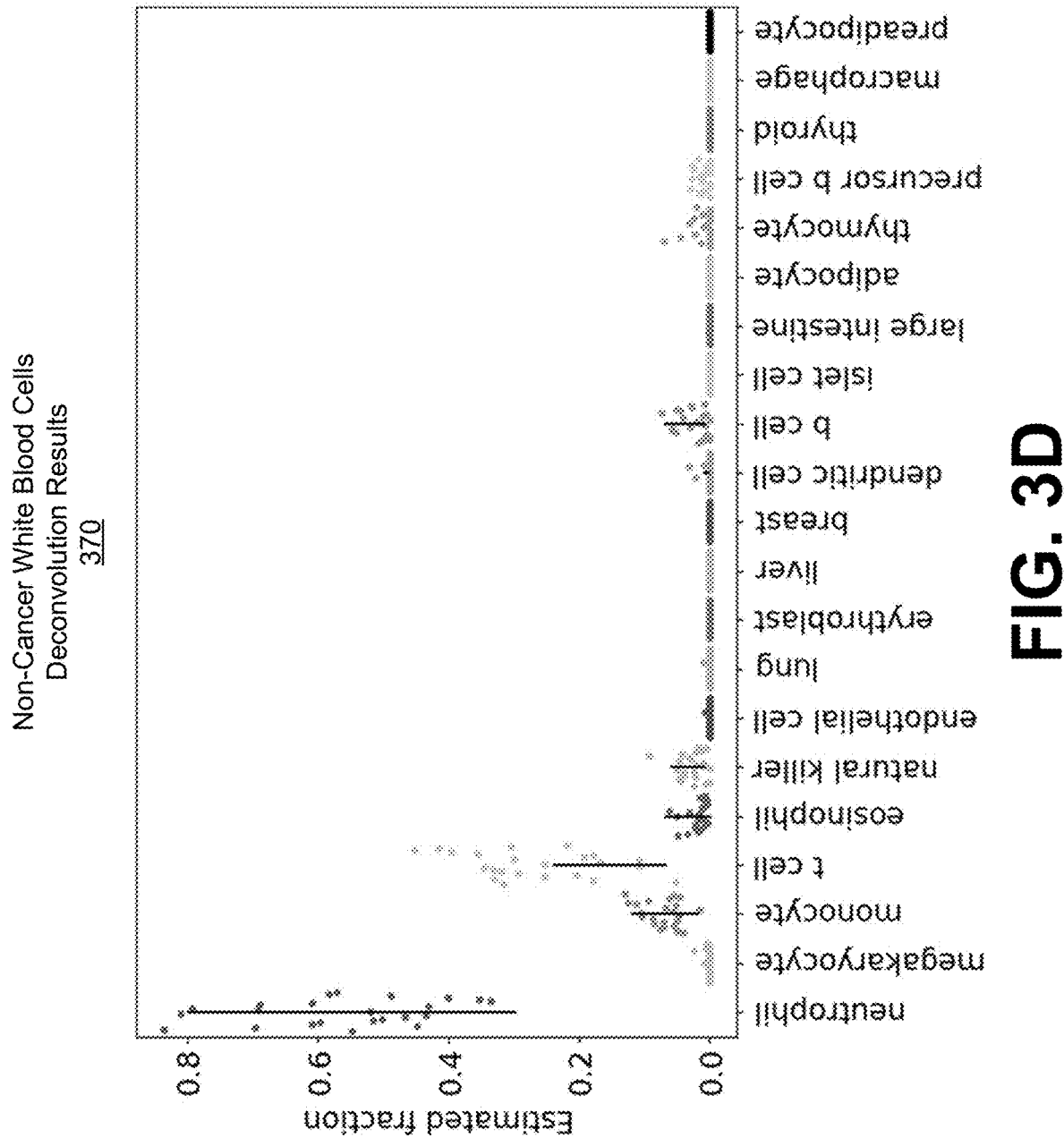
FIGS. 3D and 3E are graphs validating the deconvolution model, according to an embodiment.
Figure 3E:
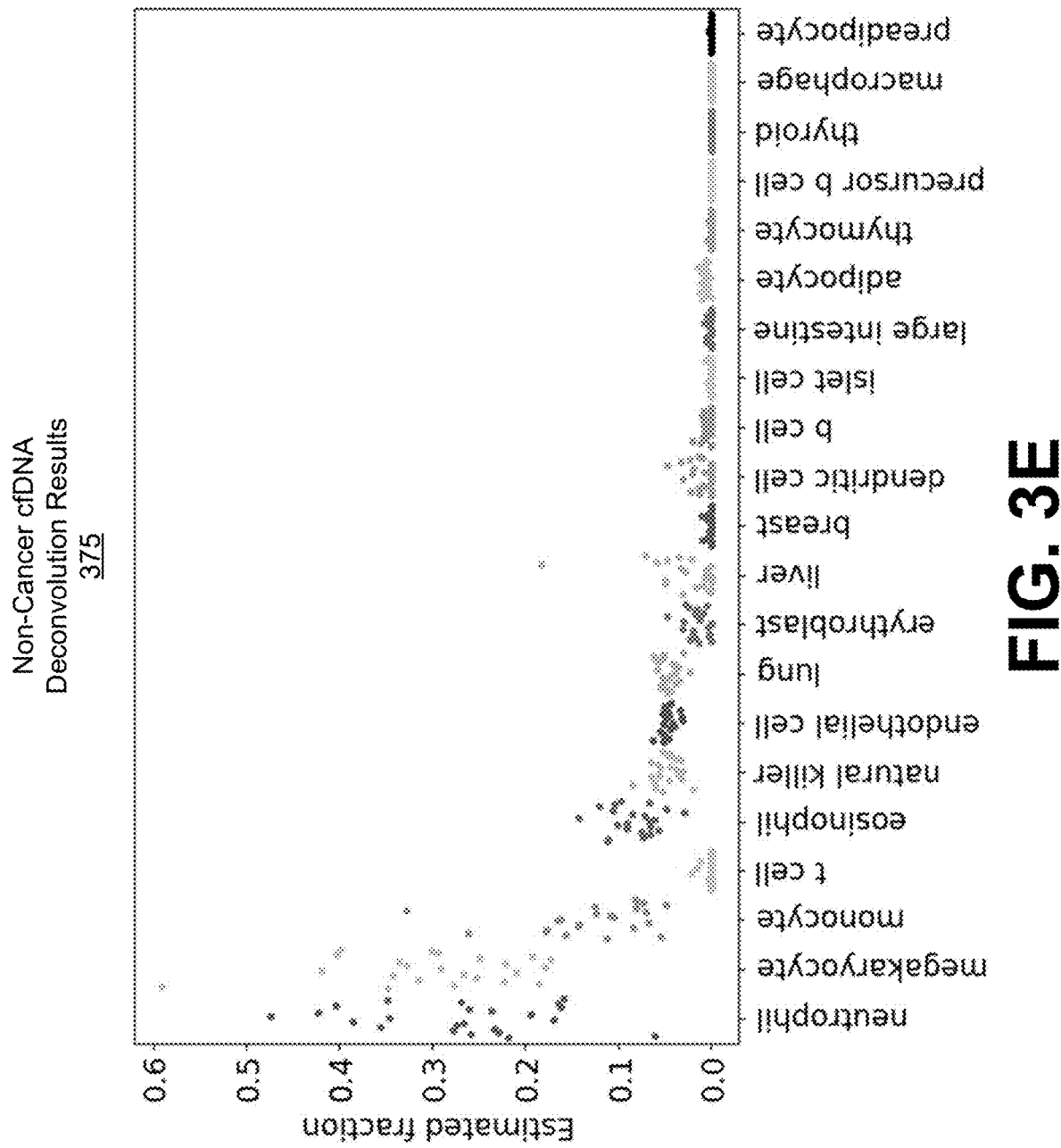

FIGS. 3D and 3E are graphs validating use of the deconvolution model to generate source of origin predictions, according to an embodiment. Along the x-axis of each graph are various source types. Along the y-axis of each graph is estimated fractions for the source predictions determined for each sample.

FIG. 3D is a graph 370 comparing source of origin predictions determined by the process 330 of FIG. 3B to clinical data from academia. The clinical data used for comparison in the example shown in FIG. 3D comes from International Human Epigenome Consortium (http://ihec-epigenomes.org/). The samples collected and deconvolved for the example shown in FIG. 3D consisted of twenty-three WBC samples obtained from twenty-three healthy individuals. These samples were used to validate the consistency and accuracy of an example deconvolution model generated described above in FIGS. 3A-3C. The clinical data are represented as black bars in the graph showing average ranges of percentages for each of the sources contributing DNA molecules to WBC samples. In particular, there are normal ranges above zero for blood related cell types including neutrophil cell type, monocyte cell type, T cell type, eosinophil cell type, natural killer cell type, dendritic cell type, and B cell type. All the remaining sources have not been shown, according to the clinical data, to significantly contribute DNA molecules to WBC samples.

Each source prediction generated by the deconvolved model is an estimated fraction of the DNA molecules in the validation sample that are predicted to originate from the corresponding source. Each source prediction is plotted as a dot above the corresponding source at the estimate fraction. In this example, twenty-three WBC samples were deconvolved to generate twenty-three corresponding source of origin predictions. Notably, of all the black bars shown from the clinical data, the source predictions of the twenty-three WBC samples covered all the black bars showing a similarity to the clinical data. The T cell type, the thymocyte cell type, and the precursor cell type had source predictions that fell beyond the normal ranges provided from the clinical data. However, the remaining sources (mainly non-blood related cell types) all had source predictions close to zero which was also corroborated by the clinical data.

FIG. 3E is a graph 375 showing source of origin predictions determined by the process 330 of FIG. 3B with cfDNA samples. The samples collected and deconvolved for the example shown in FIG. 3E consisted of fifty-five cfDNA samples obtained from fifty-five healthy individuals. These samples are used to validate the sensitivity of the deconvolution model described above in FIGS. 3A-3C in generating source predictions of various tissue types in addition to the cell types. In this example, most all of the tissue types considered had many source predictions from the fifty-five samples that were significantly above zero including lung tissue type, liver tissue type, and breast tissue type. This shows an ability to predict DNA molecule contributions from the tissue types in cfDNA samples.

Figure 3F:
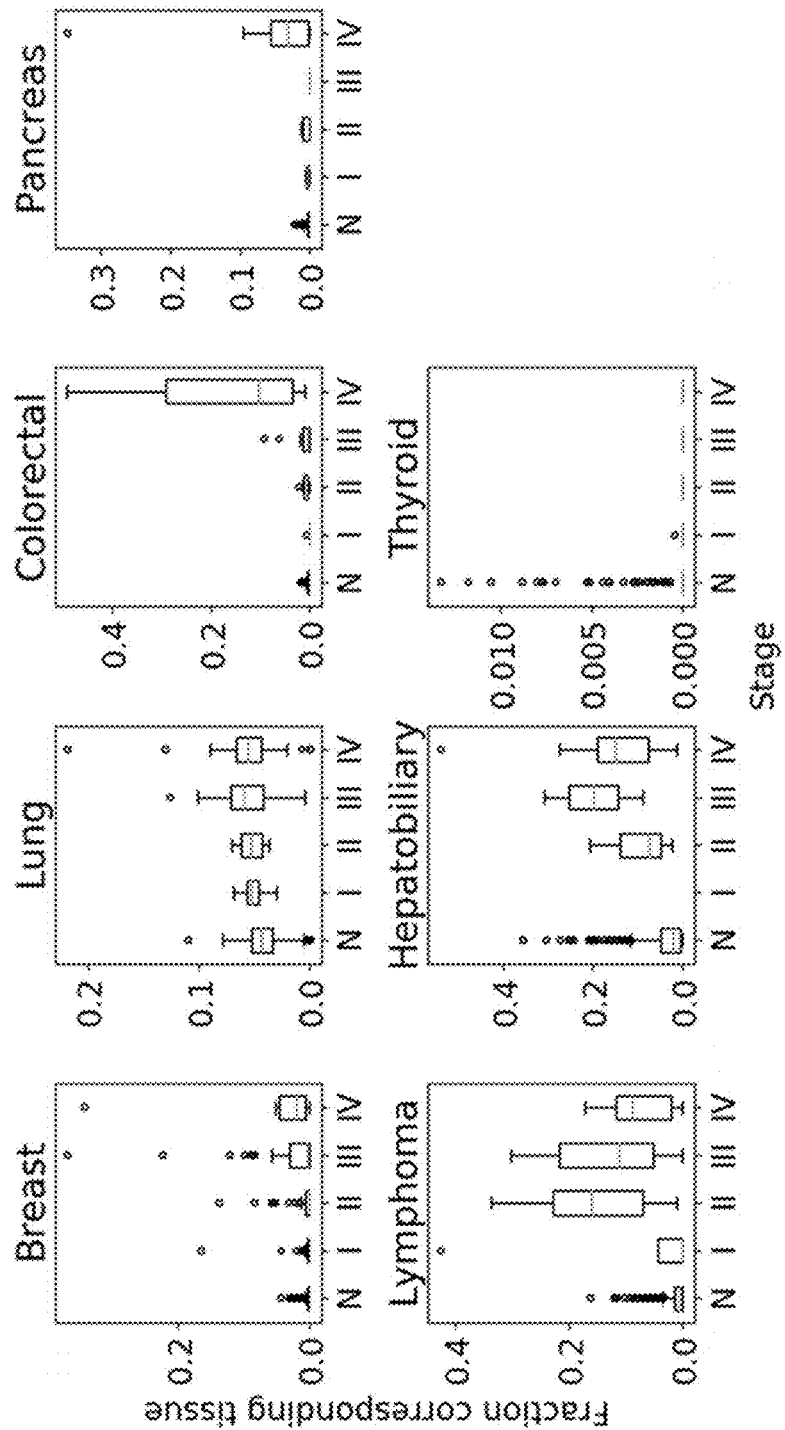
FIG. 3F is a graph showing tissue fractions of corresponding cancer types present in cfDNA over each stage of cancer, according to an embodiment.

FIG. 3F is a graph 380 showing tissue fractions from corresponding cancer types present in cfDNA over each stage of cancer, according to an embodiment. In this example, there are 7 cohorts of cancer types that each have subjects at varying stages of the cancer. The dataset used for the example shown in FIG. 3F comes from a clinical study titled The Circulating Cell-free Genome Atlas Study ("CCGA"). The CCGA study was described with Clinical Trial.gov Identifier: NCT02889978 (https://www.clinicaltrials.gov/ct2/showNCT02889978). The 7 cancer types are breast cancer, lung cancer, colorectal cancer, pancreas cancer, lymphoma cancer, hepatobiliary cancer, and thyroid cancer. In addition to the subjects, there are a number of healthy samples included in each cohort to show comparative source predictions. Along the x-axis of each graph are a healthy group and each stage of cancer in the cohort: Stage I, Stage II, Stage III, and Stage IV. Along the y-axis of each graph is estimated fractions for the source predictions determined for each sample.

In most of the cohorts, corresponding tissue contributions to cfDNA increase in latter stages of cancer. In the breast cancer cohort, there is a gradual increase of breast tissue contributions to the cfDNA from ~0 in Stage I to 0.04 in Stage IV of cancer. Similarly with the lung cancer cohort, there is a slight increase from 0.05 in Stage I of cancer to 0.06 in Stage IV of cancer. More distinctly with the colorectal cohort and the pancreas cohort, there are sharp rises in tissue contributions from Stage III of cancer to Stage IV of cancer, with both spiking from ~0 to ~0.1. Interestingly with the lymphoma cohort and the hepatobiliary cohort, significant tissue contributions were observed in Stage II of cancer, with lymphoma having the highest increase from ~0 in Stage I to ~0.18 in Stage II. Contrary to the others, the thyroid cohort had no difference in thyroid tissue contribution throughout the various stages of thyroid cancer.

IV. Cancer Classifier for Determining Cancer

IV.A. Training of Cancer Type Classifier

Figure 4:
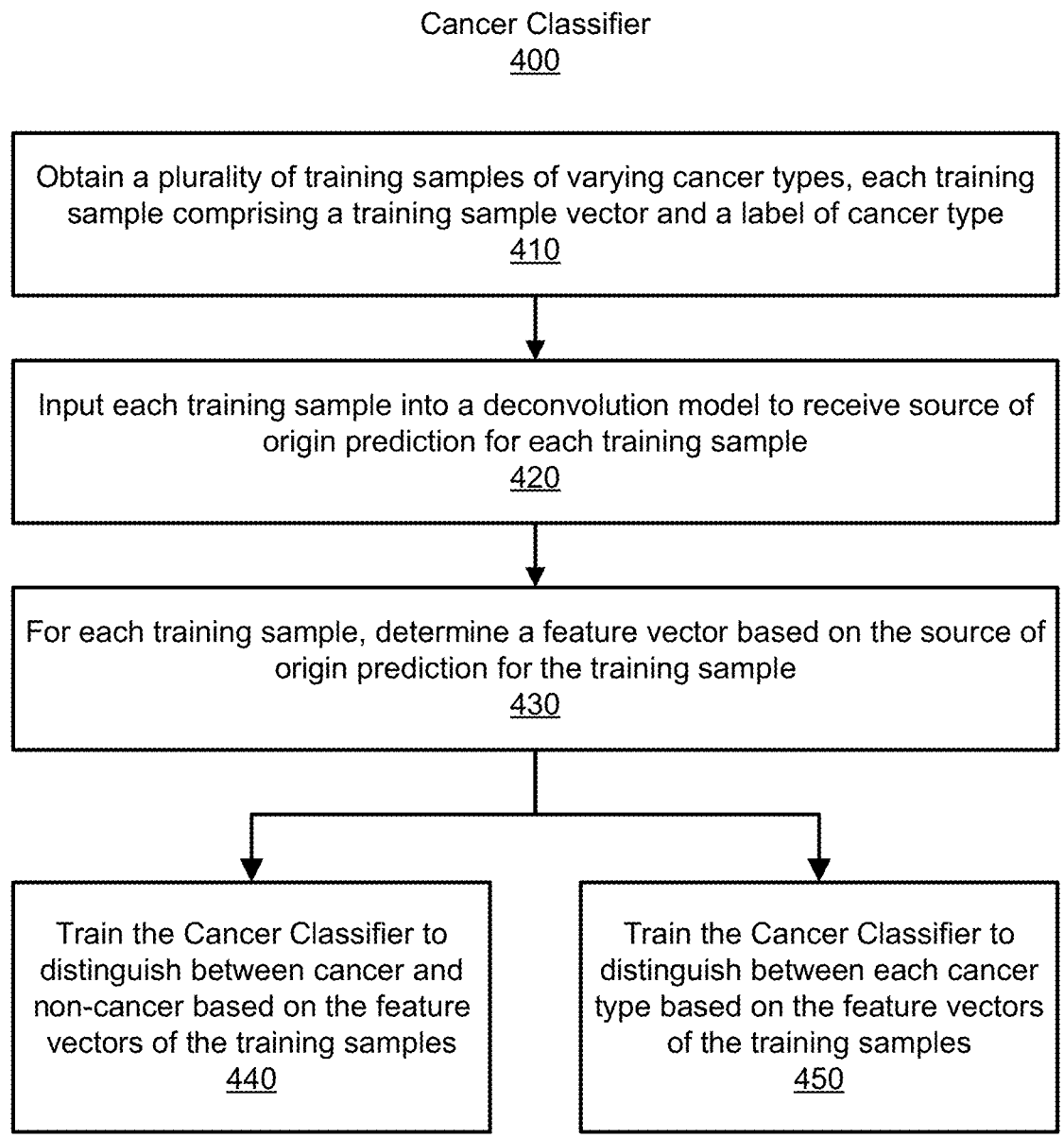
FIG. 4 is a flowchart describing a process of training a cancer classifier, according to an embodiment.

FIG. 4 is a flowchart describing a process 400 of training a cancer classifier, according to an embodiment. The cancer classifier is trained to receive a feature vector for a test sample and return a cancer prediction. The cancer classifier comprises a plurality of classification parameters and a function representing a relation between the feature vector as input and the cancer prediction as output according to the classification parameters and the input feature vector. In one embodiment, the feature vectors input into the cancer classifier are based on the source of origin predictions determined by the deconvolution model in the process 330. Prior to deployment of the cancer classifier, the analytics system trains the cancer classifier with the process 400. It should be noted that although reference is made herein to the determination of a presence or absence of cancer within a test subject, the classifiers described herein can detect a presence or absence of any disease or condition within a test subject.

The analytics system first obtains 410 a plurality of training samples each having a training sample vector and a label of cancer type. The plurality of training samples include any combination of samples from healthy individuals with a general label of "non-cancer," samples from subjects with a general label of "cancer" or a specific label (e.g., "breast cancer," "lung cancer," etc.). The training sample vector may be achieved through any combination of the processes 100 of FIG. 1A and 200 of FIG. 2.

The analytics system inputs 420 each training sample into a deconvolution model to receive a source of origin prediction for each training sample. The deconvolution model may be the one described above in Section III. Deconvolution Model for Determining Source of Origin Prediction. The source of origin prediction has a source prediction (i.e. an estimated fraction of DNA molecule contribution in the sample from the source) for a number of sources [K].

The analytics system determines 430, for each training sample, a feature vector based on the source of origin prediction for the training sample. In one embodiment, the source of origin prediction includes source predictions for sources [K] and the feature vector is the source of origin prediction. In other embodiments, the feature vector is a truncated form of the source of origin prediction. For example, one source of origin prediction may comprise source predictions for sources x, y, and z, however the classifier may be designed to predict presence/absence of cancer based on for sources x and z but not source y. Additionally or alternatively, the training samples used to train the classifier may have a predetermined source contribution, e.g., through clinical analyses, rather than having source contributions determined by the convolution model.

With the training samples, the analytics system may train the cancer classifier in multiple ways. In one embodiment, the analytics system trains 440 the cancer classifier to distinguish between cancer and non-cancer based on the feature vectors of the training samples. In this manner, the analytics system uses training samples that include both non-cancer samples from healthy individuals and cancer samples from subjects. Each training sample has one of the two labels "cancer" or non-cancer." In this embodiment, the classifier outputs a prediction score indicating the likelihood of the presence or absence of cancer.

In another embodiment, the analytics system trains 450 the cancer classifier to distinguish between various cancer types. To do so, the analytics system uses training samples that include cancer samples with various cancer types but may also include non-cancer samples. For example, the labels may be "breast cancer," "liver cancer," "lung cancer," "pancreas cancer," and "non-cancer." In this embodiment, the classifier outputs a set of prediction scores corresponding to likelihoods of a test sample having each of the cancer types. For example, the cancer classifier may return a cancer prediction including a prediction score for breast cancer, lung cancer, and no cancer. An example cancer prediction for a test sample is 65% likelihood of breast cancer, 25% likelihood of lung cancer, and 10% likelihood of non-cancer. The analytics system may further process the predictions regarding individual cancer types to generate a single cancer determination. Continuing with the example above and given the percentages, in this example the system may determine that the sample has breast cancer. It should also be noted that the multi-cancer classifier can classify a test sample and produce a score for each of the types of cancer associated with the multi-cancer classifier such that the scores are independent of each other (and thus do not necessarily add up to 100). In this embodiment, the classifier may output a 90% likelihood of breast cancer and an 80% likelihood of lung cancer, indicating that the individual associated with the test sample has more than one type of cancer (or has a cancer that has metastasized to a different location).

In both embodiments, the analytics system trains the cancer classifier by inputting each training feature vector into the cancer classifier and adjusting classification parameters so that the function accurately relates the training feature vector to its corresponding label. After inputting all training feature vectors and adjusting the classification parameters, the cancer classifier is sufficiently trained to label test samples according to their feature vector within some margin of error. The analytics system may train the cancer classifier according to any one of a number of methods. As an example, in one embodiment the binary cancer classifier is a L2-regularized logistic regression classifier that is trained using a log-loss function. As another example, in one embodiment the multi-cancer classifier is a multinomial logistic regression. In practice either type of cancer classifier may be trained using other techniques. These techniques are numerous including potential use of kernel methods, machine learning algorithms such as multilayer neural networks, etc.

IV.B. Use of Cancer Classifier

During use of the cancer classifier, the analytics system obtains a test sample of unknown cancer type. The analytics system may process the test sample comprised of DNA molecules with any combination of the processes 100 and 200 to achieve a test sample vector that may be inputted into the deconvolution model described in the process 330. With the source of origin prediction outputted by the deconvolution model according to the process 330, the analytics system determines a test feature vector for use by the cancer classifier. The analytics system then inputs the test feature vector into the cancer classifier. The cancer classifier then generates a cancer prediction based on the classification parameters trained in the process 400 and the test feature vector.

In additional embodiments, the analytics system chains a cancer classifier trained in step 440 of the process 400 with another cancer classifier trained in step 450 of the process 400. The analytics system inputs the test feature vector into the cancer classifier trained as a binary classifier in step 440 of the process 400. The analytics system receives an output of a cancer prediction. The cancer prediction may be binary as to whether the test subject likely has or likely does not have cancer. In other implementations, the cancer prediction includes prediction values that describe likelihood of cancer and likelihood of non-cancer. For example, the cancer prediction has a cancer prediction value of 85% and the non-cancer prediction value of 15%. The analytics system may determine the test subject to likely have cancer. Once the analytics system determines a test subject is likely to have cancer, the analytics system may input the test feature vector into a multiclass cancer classifier trained in step 450 of the process 400 to distinguish between different cancer types. The multiclass cancer classifier receives the test feature vector and returns a cancer prediction of a cancer type of the plurality of cancer types. For example, the multiclass cancer classifier provides a cancer prediction specifying that the test subject is most likely to have ovarian cancer. In another implementation, the multiclass cancer classifier provides a prediction value for each cancer type of the plurality of cancer types. For example, a cancer prediction may include a breast cancer type prediction value of 40%, a colorectal cancer type prediction value of 15%, and a liver cancer prediction value of 45%.

In some embodiments, in response to the cancer classifier outputting a cancer prediction for a test sample (e.g., either the likelihood of the presence or absence of cancer generally, or the likelihood of the presence or absence of a particular type of cancer), the prediction can be clinically verified. For instance, an individual predicted to have lung cancer can be diagnosed as having lung cancer or not having lung cancer by a physician, or an individual predicted to be cancer-free can be diagnosed with cancer by a physician. In response to the verification or contradiction of the cancer prediction outputted by the cancer classifier, the feature vector associated with the test sample can be added to the training sample set with a label representative of the verification or contradiction (e.g., the feature vector can be labeled "lung cancer," "non-cancer", and the like). The classifier can then be retrained using the updated training sample set in order to improve the performance of the classifier in subsequent applications.

IV.C. Example Results of Cancer Classifier

Figure 6A:
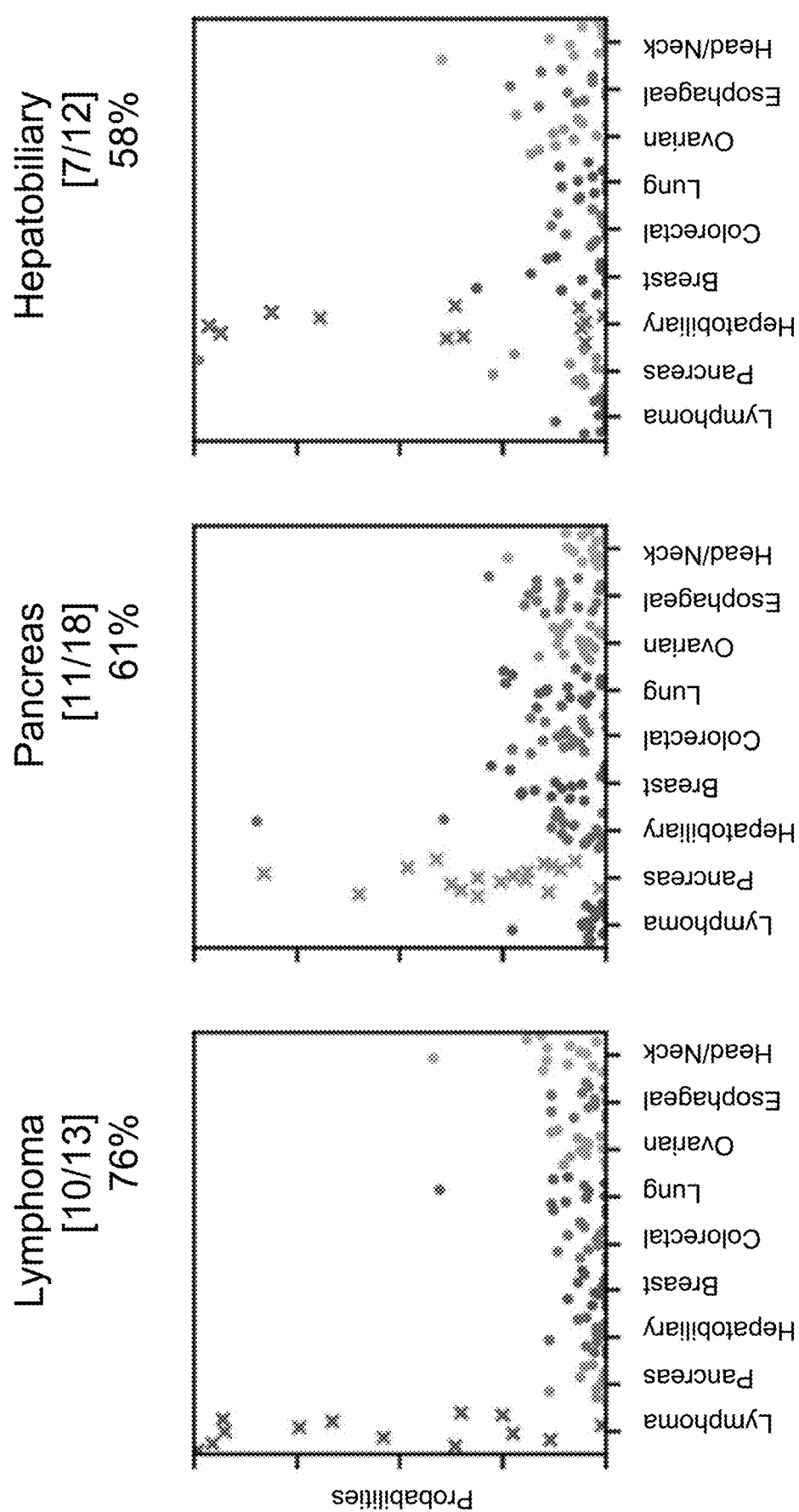
FIG. 6A-6C illustrate many graphs showing cancer prediction accuracy of the cancer classifier for various types, according to an embodiment.
Figure 6B:
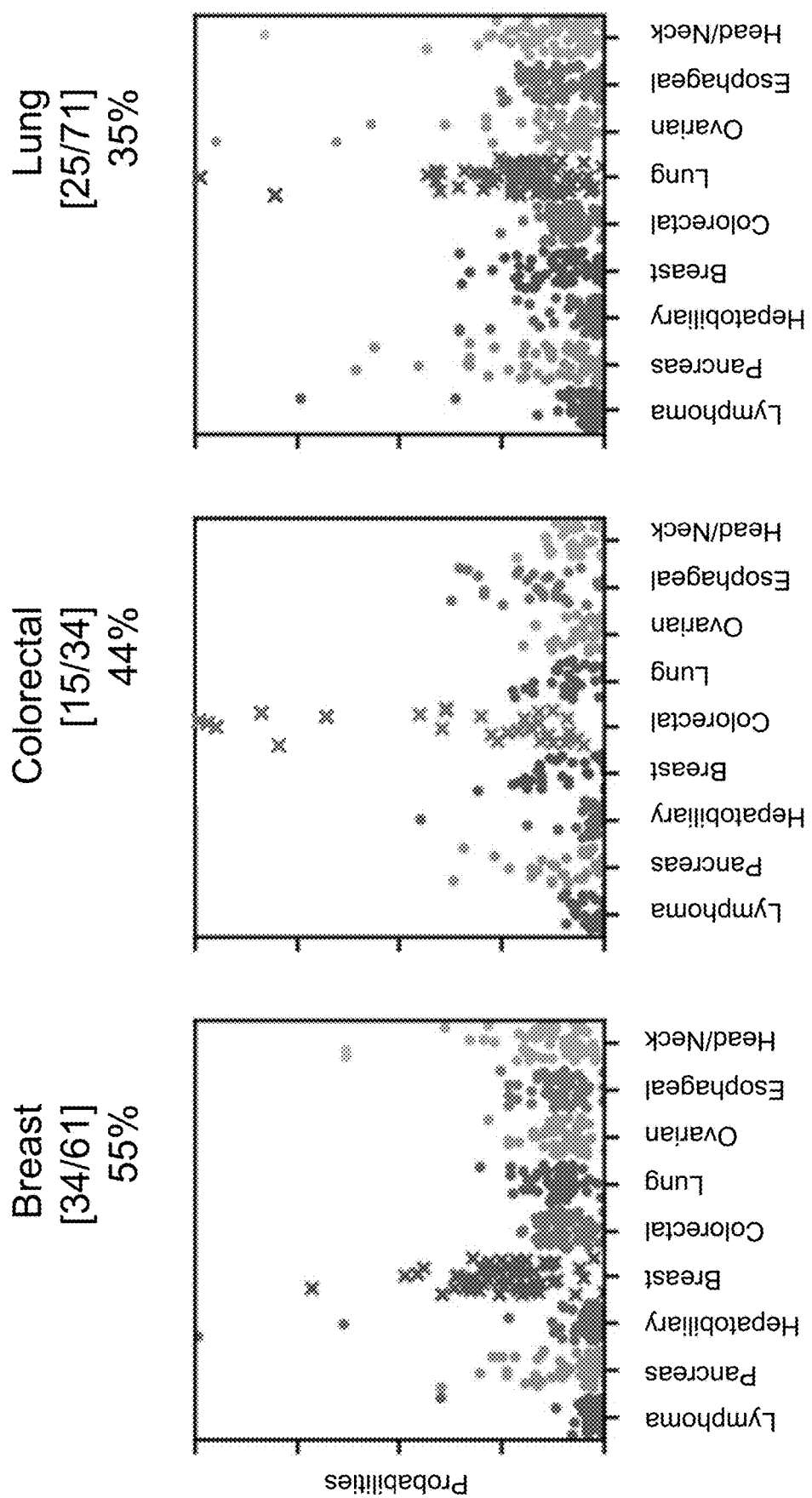
Figure 6C:
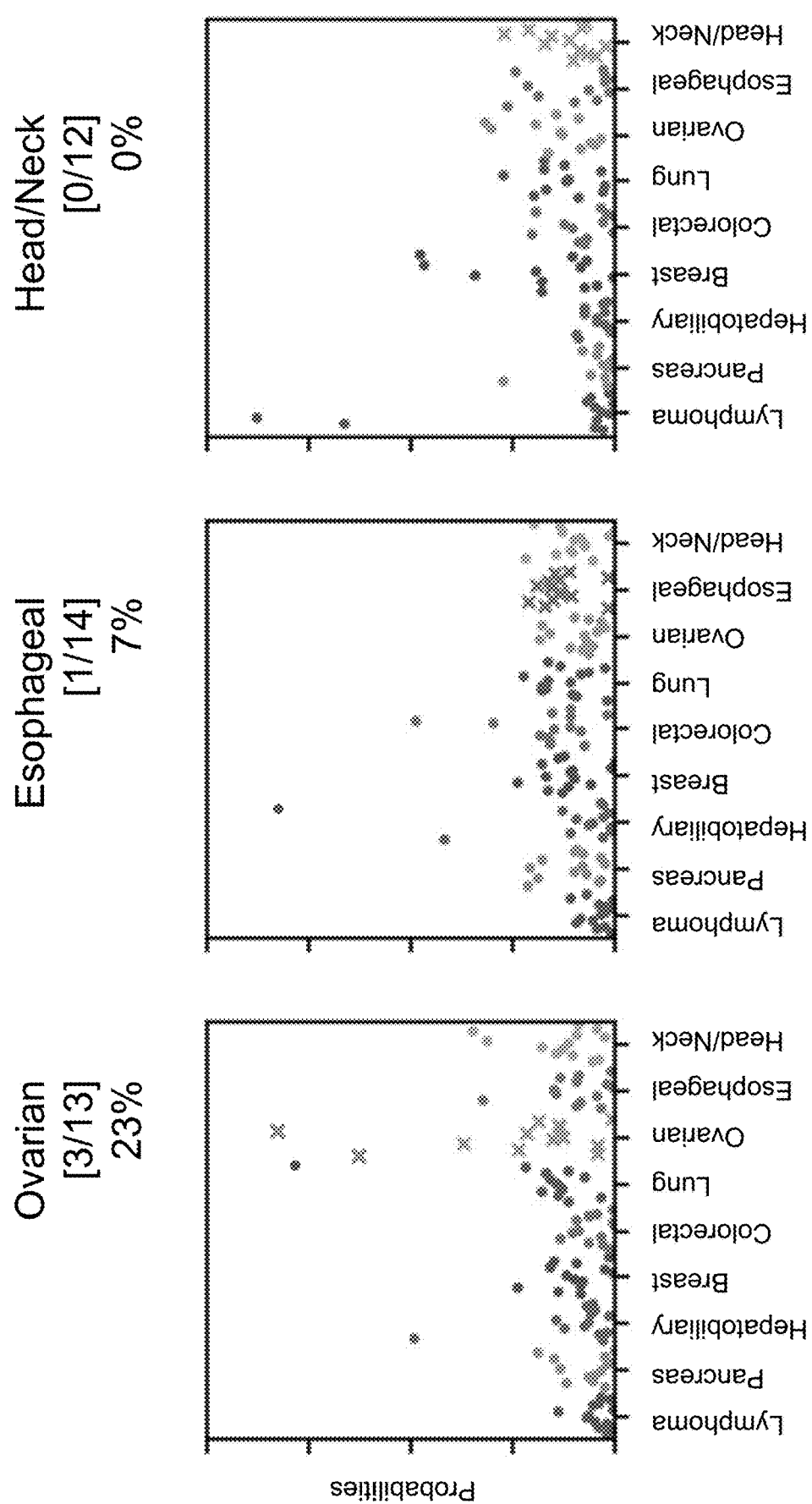

FIGS. 6A-6C illustrate many graphs showing cancer prediction accuracy of the cancer classifier for various cancer types, according to an embodiment. In one embodiment, the cancer classifier is the one described above. The cancer classifier in this example is configured in the second manner to provide cancer predictions from a group of nine different cancer types: lymphoma cancer type, pancreas cancer type, hepatobiliary cancer type, breast cancer type, colorectal cancer type, lung cancer type, ovarian cancer type, esophageal cancer type, and head/neck cancer type. The samples used in this example were from subjects known to have each of the cancer types. For example a cohort of lymphoma cancer type samples were used to validate the cancer classifier's accuracy in calling the lymphoma cancer type.

For the lymphoma cancer type, the pancreas cancer type, and the hepatobiliary cancer type (shown in FIG. 6A), the cancer classifier was between ~60-75% accurate in calling those cancer types. In particular, the cancer classifier had an accuracy of 76% for the lymphoma cancer type, accurately predicting 10 out of 13 cancer samples. The cancer classifier had an accuracy of 61% for the pancreas cancer type, accurately predicting 11 out of 18 cancer samples. The cancer classifier had an accuracy of 58% for the hepatobiliary cancer type, accurately predicting 7 out of 12 cancer samples. For these cancer types, the training samples used to train the cancer classifier had source predictions that included cell type sources corresponding to the cancer types. For example, lymphocyte cell type corresponding to lymphoma cancer, B cell type and islet cell type corresponding to pancreas cancer, and liver tissue type and/or hepatocyte cell type correspond to hepatobiliary cancer were included in the sources deconvolved for by the deconvolution model (e.g., the deconvolution model described in Section III).

For the breast cancer type, the colorectal type, and the lung type (shown in FIG. 6B), the cancer classifier was between ~35-55% accurate in calling those cancer types. In particular, the cancer classifier had an accuracy of 55% for the breast cancer type, accurately predicting 34 out of 61 cancer samples. The cancer classifier had an accuracy of 44% for the colorectal cancer type, accurately predicting 15 out of 34 cancer samples. The cancer classifier had an accuracy of 35% for the lung cancer type, accurately predicting 25 out of 71 cancer samples. For these cancer types, the training samples used to train the cancer classifier had source predictions that included tissue type sources corresponding to the cancer types. For example, breast tissue type corresponding to breast cancer, large intestine tissue type corresponding to colorectal cancer, and lung tissue type corresponding to lung cancer were included in the sources deconvolved for by the deconvolution model (e.g., the deconvolution model described in Section III). Notably, the cancer types called with only corresponding tissue type sources had less accuracy than the cancer types called with cell type sources, pointing to a better specificity with cell type sources used in the feature vector for the cancer classifier.

Finally, for the remaining cancer types shown in FIG. 6C (ovarian cancer type, esophageal cancer type, and head/neck cancer type), the cancer classifier was between ~0-20% accurate in calling the remaining cancer types. In particular, the cancer classifier had an accuracy of 23% for the ovarian cancer type (3 out of 13), 7% for the esophageal cancer type (1 out of 14), and 0% for the head/neck cancer type (0 out of 12). This may have been a result of lack of training samples of corresponding sources used in training the deconvolution model which meant a lack in source predictions for those corresponding sources as well.

V. Computing Machine Architecture

Figure 7:
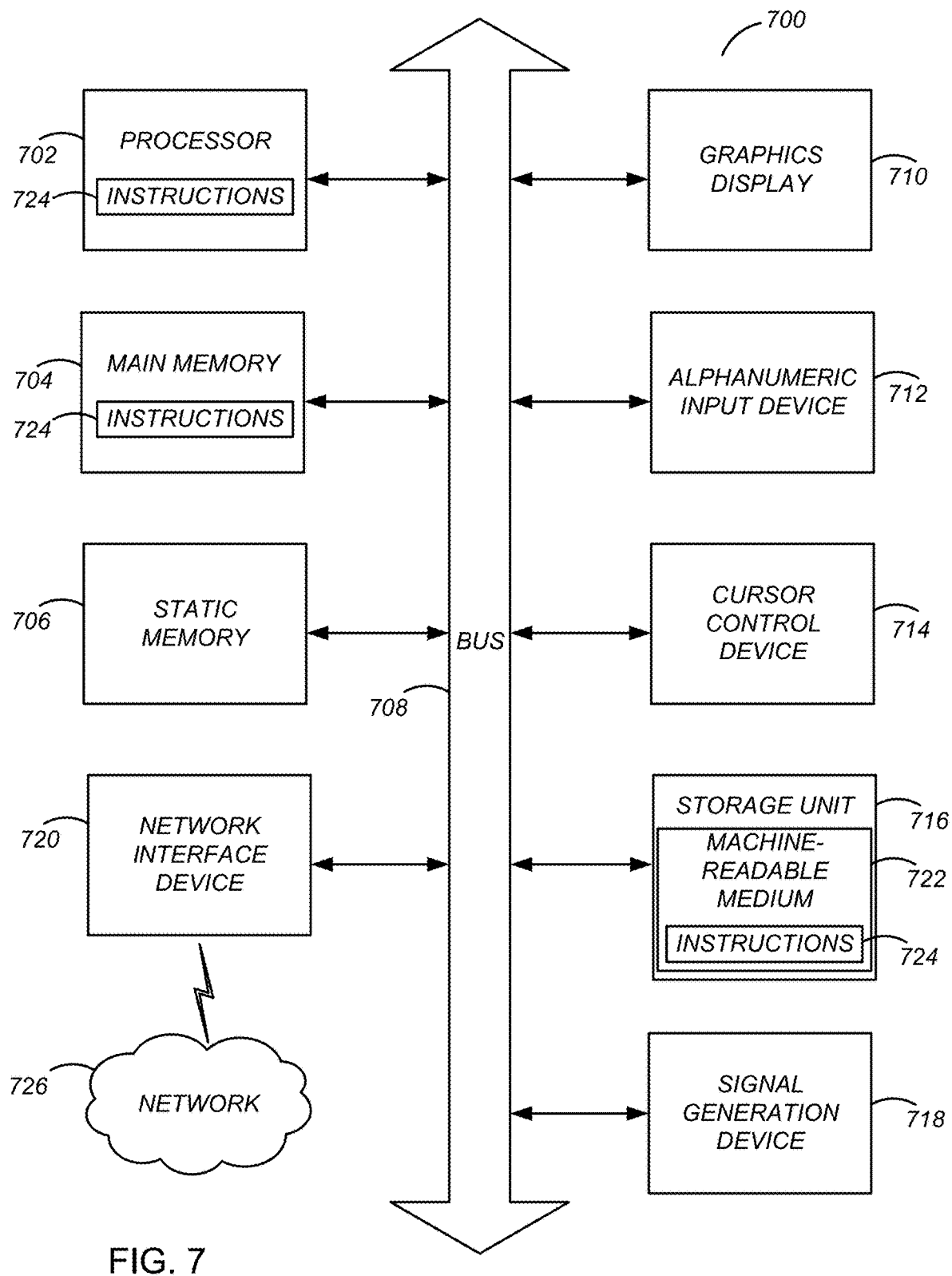
FIG. 7 shows a schematic of an example computer system for implementing various methods of the processes described herein, according to an embodiment.

FIG. 7 shows a schematic of an example computer system for implementing various methods of the processes described herein, according to an embodiment. In particular, FIG. 7 is a block diagram illustrating components of an example computing machine that is capable of reading instructions from a computer-readable medium and executing them using a processor (or controller). A computer as described herein may include a single computing machine as shown in FIG. 7, a virtual machine, a distributed computing system that includes multiples nodes of computing machines shown in FIG. 7, or any other suitable arrangement of computing devices.

By way of example, FIG. 7 shows a diagrammatic representation of a computing machine in the example form of a computer system 700 within which instructions 724 (e.g., software, program code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 7 may correspond to any software, hardware, or combined components (e.g., those shown in FIGS. 5A and 5B or a processing unit described herein), including but not limited to any engines, modules, computing server, machines that are used to perform one or more processes described herein. While FIG. 7 shows various hardware and software elements, each of the components described herein may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 724 that specify actions to be taken by that machine. Further, while only a single machine is illustrated, the term "machine" and "computer" may also be taken to include any collection of machines that individually or jointly execute instructions 724 to perform any one or more of the methodologies discussed herein.

The example computer system 700 includes one or more processors 702 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 700 may also include a memory 704 that store computer code including instructions 724 that may cause the processors 702 to perform certain actions when the instructions are executed, directly or indirectly by the processors 702. Instructions can be any directions, commands, or orders that may be stored in different forms, such as equipment-readable instructions, programming instructions including source code, and other communication signals and orders. Instructions may be used in a general sense and are not limited to machine-readable codes.

One or more methods described herein improve the operation speed of the processors 702 and reduces the space required for the memory 704. For example, the machine learning methods described herein reduces the complexity of the computation of the processors 702 by applying one or more novel techniques that simplify the steps in training, reaching convergence, and generating results of the processors 702. The algorithms described herein also may reduce the size of the models and datasets to reduce the storage space requirement for memory 704.

The performance of certain of the operations may be distributed among the more than one processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations. Even though in the specification or the claims may refer some processes to be performed by a processor, this should be construed to include a joint operation of multiple distributed processors.

The computer system 700 may include a main memory 704, and a static memory 706, which are configured to communicate with each other via a bus 708. The computer system 700 may further include a graphics display unit 710 (e.g., a plasma display panel (PDP), a liquid crystal display (LCD), a projector, or a cathode ray tube (CRT)). The graphics display unit 710, controlled by the processors 702, displays a graphical user interface (GUI) to display one or more results and data generated by the processes described herein. The computer system 700 may also include alpha-numeric input device 712 (e.g., a keyboard), a cursor control device 714 (e.g., a mouse, a trackball, a joystick, a motion sensor, or other pointing instrument), a storage unit 716 (a hard drive, a solid state drive, a hybrid drive, a memory disk, etc.), a signal generation device 718 (e.g., a speaker), and a network interface device 720, which also are configured to communicate via the bus 708.

The storage unit 716 includes a computer-readable medium 722 on which is stored instructions 724 embodying any one or more of the methodologies or functions described herein. The instructions 724 may also reside, completely or at least partially, within the main memory 704 or within the processor 702 (e.g., within a processor's cache memory) during execution thereof by the computer system 700, the main memory 704 and the processor 702 also constituting computer-readable media. The instructions 724 may be transmitted or received over a network 726 via the network interface device 720.

While computer-readable medium 722 is shown in an example embodiment to be a single medium, the term "computer-readable medium" should be taken to include a single non-transitory medium or multiple media (e.g., a centralized or distributed database, or associated caches and servers) able to store instructions (e.g., instructions 724). The computer-readable medium may include any medium that is capable of storing instructions (e.g., instructions 724) for execution by the processors (e.g., processors 702) and that cause the processors to perform any one or more of the methodologies disclosed herein. The computer-readable medium may include, but not be limited to, data repositories in the form of solid-state memories, optical media, and magnetic media.

VI. Additional Considerations

The foregoing detailed description of embodiments refers to the accompanying drawings, which illustrate specific embodiments of the present disclosure. Other embodiments having different structures and operations do not depart from the scope of the present disclosure.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Any of the steps, operations, or processes described herein may be performed or implemented with one or more hardware or software modules of the apparatus, alone or in combination with other devices. In one embodiment, a software module is implemented with a computer program product comprising a computer-readable medium containing computer program code, which can be executed by a computer processor for performing any or all of the steps, operations, or processes described.

What is claimed is:

1. A method for determining a cancer type from a test sample comprising a set of deoxyribonucleic acid (DNA) fragments from a test subject, the method comprising:

accessing a data set derived from the test sample, the data set comprising the set of DNA fragments, each DNA fragment including one or more CpG sites, wherein a methylation state at each of the one or more CpG sites has been determined to be methylated or unmethylated;

generating a test sample vector comprising, for each of a plurality of CpG sites, a site methylation metric for the DNA fragments from the test sample that are methylated at that CpG site;

inputting the test sample vector into a trained deconvolution model to generate a source of origin prediction comprising a plurality of values, each value indicating a fraction of the DNA fragments predicted to have originated from one of a plurality of sources including tissue types and cell types, wherein the trained deconvolution model is trained on a training data set comprising training samples that are obtained from healthy subjects;

inputting the source of origin prediction for the test sample into a trained cancer classifier to generate a cancer prediction comprising a plurality of cancer prediction values, each cancer prediction value describing a likelihood the test subject has a particular cancer type of a plurality of cancer types, wherein the trained cancer classifier is trained by:
    accessing an additional training data set comprising training samples obtained from healthy subjects and training samples obtained from subjects diagnosed with cancer, wherein each training sample in the additional training data set includes a methylation state at each of one or more CpG sites on each of a set of DNA fragments,
    generating, for each training sample in the additional training data set, a training sample vector comprising, for each of the plurality of CpG sites, a site methylation metric for the DNA fragments from the training sample that are methylated at that CpG site,
    inputting each training sample vector into the trained deconvolution model to generate a corresponding source of origin prediction for the training sample, and
    training the cancer classifier with the source of origin predictions and the cancer types of the training samples from the additional training data set; and determining whether the test subject has a first cancer type from the plurality of cancer types based on the cancer prediction.

2. The method of claim 1,
wherein the cancer classifier comprises a second function representing a relation between the source of origin prediction received as input and the cancer prediction provided as output based on classification parameters and the second function.

3. The method of claim 2, wherein the plurality of cancer types include a breast cancer type, a colorectal cancer type, an esophageal cancer type, a head/neck cancer type, a hepatobiliary cancer type, a lung cancer type, a lymphoma cancer type, an ovarian cancer type, a pancreas cancer type, an anorectal cancer type, a cervical cancer type, a gastric cancer type, a leukemia cancer type, a multiple myeloma cancer type, a prostate cancer type, a renal cancer type, a thyroid cancer type, a uterine cancer type, a brain cancer type, a sarcoma cancer type, a neuroendocrine cancer type.

4. The method of claim 2, wherein the trained cancer classifier is a logistic regression classifier or a multinomial logistic regression classifier.

5. The method of claim 1, wherein the trained deconvolution model comprises:
    a plurality of methylation parameters, wherein the methylation parameters comprise a methylation level at each of the plurality of CpG sites for each of the plurality of sources, and
    a function representing a relation between the test sample vector received as input and the source of origin prediction generated as output based on the test sample vector and the plurality of methylation parameters.

6. The method of claim 5, wherein the plurality of methylation parameters is generated from a first set of training samples from the plurality of sources.

7. The method of claim 6, wherein the first set of training samples is obtained from healthy individuals.

8. The method of claim 6, wherein the methylation parameters are trained on information comprising:
    the first set of training samples from the plurality of sources, each of the training samples from a source of the plurality of sources comprising:
        a training sample vector comprising a plurality of methylation metrics for each of the plurality of CpG sites, and
        an identification of the source the training sample originates from.

9. The method of claim 8, wherein the trained deconvolution model is trained by applying a minimization function to reduce a least squares difference between each training sample and a matrix product of the methylation parameters and a vector of values representing the source of the training sample.

10. The method of claim 1, wherein the CpG sites used in the trained deconvolution model are identified according to:
    for each CpG site of an initial set of CpG sites, computing information gain for deriving one or more sources of the plurality of sources; and
    identifying a plurality of informative CpG sites to be used in the trained model from the initial set of CpG sites based on the computed information gain of each CpG site.

11. The method of claim 10, further comprising:
    ranking the initial set of CpG sites based on the computed information gain, and
    wherein identifying the informative CpG sites to be used in the trained model is based on the ranking of the initial set of CpG sites.

12. The method of claim 1, wherein the plurality of sources comprises any combination of a large intestine tissue type, a breast tissue type, a thyroid tissue type, a lung tissue type, a bladder tissue type, a cervix tissue type, and a colorectal tissue type.

13. The method of claim 12, wherein the plurality of sources further comprises any combination of an esophagus tissue type, a gastric tissue type, a tonsil tissue type, a liver tissue type, a white blood cell tissue type, an ovary tissue type, a pancreas tissue type, a prostate tissue type, a kidney tissue type, a thyroid tissue type, and a uterus tissue type.

14. The method of claim 1 wherein the plurality of sources comprises any combination of a B cell type, a dendritic cell type, an endothelial cell type, an eosinophil cell type, an erythroblast cell type, a macrophage cell type, a megakaryocyte cell type, a monocyte cell type, a natural killer cell type, a neutrophil cell type, a precursor B cell type, a T cell type, a thymocyte cell type, an adipocyte cell type, a hepatocyte cell type, an islet cell type, and a preadipocyte cell type.

15. The method of claim 1, wherein the plurality of sources comprises any combination of a large intestine tissue type, a breast tissue type, a thyroid tissue type, a lung tissue type, a bladder tissue type, a cervix tissue type, a colorectal tissue type, an esophagus tissue type, a gastric tissue type, a tonsil tissue type, a liver tissue type, a white blood cell tissue type, an ovary tissue type, a pancreas tissue type, a prostate tissue type, a kidney tissue type, a thyroid tissue type, a uterus tissue type, a B cell type, a dendritic cell type, an endothelial cell type, an eosinophil cell type, an erythroblast cell type, a macrophage cell type, a megakaryocyte cell type, a monocyte cell type, a natural killer cell type, a neutrophil cell type, a precursor B cell type, a T cell type, a thymocyte cell type, an adipocyte cell type, a hepatocyte cell type, an islet cell type, and a preadipocyte cell type.

16. The method of claim 1, wherein each DNA fragment of a plurality of the set of fragments is an anomalous fragment, the method further comprising:
   filtering an initial set of fragments with p-value filtering to generate the set of anomalous fragments, the filtering comprising removing fragments from the initial set having below a threshold p-value with respect to others to produce the set of anomalous fragments.

17. The method of claim 16, wherein each fragment of the plurality of the set of fragments is also hypomethylated or hypermethylated such that the fragment includes at least a threshold number of CpG sites with more than a threshold percentage of the CpG sites being unmethylated or with more than the threshold percentage of the CpG sites being methylated, respectively.

* * * * *